United States Patent
Charles et al.

(10) Patent No.: US 10,407,711 B2
(45) Date of Patent: *Sep. 10, 2019

(54) METHOD FOR OBTAINING PEPTIDES

(71) Applicant: bioMérieux, Marcy l'Etoile (FR)

(72) Inventors: Marie-Hélène Charles, Condrieu (FR); Jean-Philippe Charrier, Tassin la Demi-Lune (FR); Myriam-Laure Cubizolles, Corenc (FR); Agnès Dupont-Filliard, Les Adrets (FR); Véronique Lanet, Lyons (FR); Florence Rivera, Champagnier (FR); Laurent Veron, Villeurbanne (FR); Lucie Baujard-Lamotte, Paris (FR); Christine Peponnet, Seyssinet (FR)

(73) Assignee: bioMérieux, Marcy l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,615

(22) Filed: Dec. 18, 2018

(65) Prior Publication Data

US 2019/0112632 A1 Apr. 18, 2019

Related U.S. Application Data

(63) Continuation of application No. 14/398,339, filed as application No. PCT/EP2013/059192 on May 2, 2013, now Pat. No. 10,190,148.

(30) Foreign Application Priority Data

May 3, 2012 (FR) ..................................... 12 54090

(51) Int. Cl.
| | | |
|---|---|---|
| C12Q 1/37 | (2006.01) | |
| C07K 1/12 | (2006.01) | |
| C12N 13/00 | (2006.01) | |
| C07K 1/107 | (2006.01) | |
| C07K 1/36 | (2006.01) | |
| G01N 33/68 | (2006.01) | |

(52) U.S. Cl.
CPC .............. *C12Q 1/37* (2013.01); *C07K 1/1077* (2013.01); *C07K 1/12* (2013.01); *C07K 1/36* (2013.01); *C12N 13/00* (2013.01); *G01N 33/6848* (2013.01)

(58) Field of Classification Search
None
See application file for complete search history.

(56) References Cited

U.S. PATENT DOCUMENTS

| | | |
|---|---|---|
| 6,329,137 B1 | 12/2001 | Cromlish et al. |
| 7,622,273 B2 | 11/2009 | Gibbs |
| 2004/0229283 A1 | 11/2004 | Gygi et al. |
| 2010/0297667 A1 | 11/2010 | Ryu et al. |
| 2011/0318779 A1 | 12/2011 | Shin et al. |

FOREIGN PATENT DOCUMENTS

| | | |
|---|---|---|
| WO | WO-02/10333 A1 | 2/2002 |
| WO | WO-2005/098071 A1 | 10/2005 |
| WO | WO-2006/031063 A1 | 3/2006 |
| WO | WO-2006/128492 A1 | 12/2006 |
| WO | WO-2008/066629 A2 | 6/2008 |
| WO | WO-2008/128029 A2 | 10/2008 |
| WO | WO-2008/145763 A1 | 12/2008 |
| WO | WO-2009/072728 A1 | 6/2009 |
| WO | WO-2009/082044 A1 | 7/2009 |
| WO | WO-2011/130521 A1 | 10/2011 |

OTHER PUBLICATIONS

Santos, H.M., et al., "An improved clean sonoreactor-based method for protein identification by mass spectrometry-based techniques", Talanta, Elsevier, Amsterdam, NL, vol. 77, No. 2, Dec. 15, 2008, pp. 870-875.
Santos, H.M., et al., "Ultrasonic multiprobe as a new tool to overcome the bottleneck of throughput in workflows for protein identification relaying on ultrasonic energy", Talanta, Elsevier, Amsterdam, NL, vol. 81, No. 1-2, Apr. 15, 2010, pp. 55-62.
Espen, J., "International Search Report" for PCT/EP2013/05912, dated Jul. 12, 2013, 7 pages.
Alexander, Elizabeth, et al.; "Metabolomics-Based Approach to Antibiotic Resistance in *Staphylococcus aureus* "; 2009; 1 page.
Chapin, Kimberle C.; "Principles of Stains and Media"; Manual of Clinical Microbiology, vol. 1, Section III; Chapter 14; 9th Edition; 2007; pp. 182-191.
Carroll, Karen C., et al.; "Manual and Automated Systems for Detection and Identification of Microorganisms"; Manual of Clinical Microbiology, vol. 1, Section III; Chapter 15; 9th Edition; 2007; pp. 192-217.
Nolte, Frederick S., et al.; "Molecular Detection and Identification of Microorganisms"; Manual of Clinical Microbiology, vol. 1, Section III; Chapter 16; 9th Edition; 2007; pp. 218-244.
Chapin, Kimberle C., et al.; "Reagents, Stains, and Media: Bacteriology"; Manual of Clinical Microbiology, vol. 1, Section IV; Chapter 21; 9th Edition; 2007; pp. 334-364.
Chapin, Kimberle C.; "Reagents, Stains, Media, and Cell Lines: Virology"; Manual of Clinical Microbiology, vol. 2, Section VI; Chapter 81; 9th Edition; 2007; pp. 1297-1303.
Landry, Marie Louise, et al.; "Algorithms for Detection and Identification of Viruses"; Manual of Clinical Microbiology, vol. 2, Section VI; Chapter 82; 9th Edition; 2007; pp. 1304-1307.
LaRocco, Mark T.; "Reagents, Stains, and Media: Mycology"; Manual of Clinical Microbiology, vol. 2, Section VIII; Chapter 117; 9th Edition; 2007; pp. 1737-1744.
Sharp, Susan E.; "Reagents, Stains, and Media: Parasitology"; Manual of Clinical Microbiology, vol. 2, Section X; Chapter 134; 9th Edition; 2007; pp. 2013-2019.
Garcia, Lynne S., et al.; "Algorithms for Detection and Identification of Parasites"; Manual of Clinical Microbiology, vol. 2, Section X; Chapter 135; 9th Edition; 2007; pp. 2020-2039.

(Continued)

*Primary Examiner* — Thane Underdahl
(74) *Attorney, Agent, or Firm* — Winstead PC

(57) ABSTRACT

The present invention relates to a method of obtaining peptides from procaryotic and/or eucaryotic cells.

16 Claims, 11 Drawing Sheets

(56) References Cited

OTHER PUBLICATIONS

Chen, Wei-Jen, et al.; "Functional Nanoparticle-Based Proteomic Strategies for Characterization of Pathogenic Bacteria"; Analytical Chemistry, vol. 80, No. 24; Dec. 15, 2008; pp. 9612-9621.

Fortin, Tanguy, et al.; "Clinical Quantitation of Prostate-Specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests"; Molecular & Cellular Proteomics 8.5; Dec. 8, 2008; pp. 1006-1015.

Keshishian, Hasmik, et al.; "Quantitative, Multiplexed Assays for Low Abundance Proteins in Plasma by Targeted Mass Spectrometry and Stable Isotope Dilution"; Mol Cell Proteomics, vol. 6, No. 12; Dec. 2007; pp. 2212-2229.

Fusaro, Vincent A., et al.; "Prediction of High-Responding Peptides for Targeted Protein Assays by Mass Spectrometry"; Nature Biotechnology, vol. 27, No. 2; Feb. 2009; pp. 190-198.

Mead, Jennifer A., et al.; "MRMaid, the Web-Based Tool for Designing Multiple Reaction Monitoring (MRM) Transitions"; Molecular & Cellular Proteomics 8.4; Nov. 15, 2008; pp. 696-705.

Desiere, Frank, et al.; "The PeptideAtlas Project"; Nucleic Acids Research, vol. 34, Database issue; 2006; pp. D655-D658.

Vaidyanathan, Seetharaman, et al.; "Discrimination of Aerobic Endospore-Forming Bacteria via Electrospray-Ionization Mass Spectrometry of Whole Cell Suspensions"; Analytical Chemistry, vol. 73, No. 17; Sep. 1, 2001; pp. 4134-4144.

Everley, Robert A., et al.; "Characterization of Clostridium Species Utilizing Liquid Chromatography/Mass Spectrometry of Intact Proteins"; Journal of Microbiological Methods, vol. 77; Feb. 6, 2009; pp. 152-158.

Claydon, Martin A., et al.; "The Rapid Identification of Intact Microorganisms using Mass Spectrometry"; Nature Biotechnology, vol. 14; Nov. 1996; pp. 1584-1586.

Krishnamurthy, Thaiya, et al.; "Rapid Identification of Bacteria by Direct Matrix-Assisted Laser Desorption/Ionization Mass Spectrometric Analysis of Whole Cells"; Rapid Communications in Mass Spectrometry, vol. 10; 1996; pp. 1992-1996.

Manes, Nathan P., et al.; "Targeted Protein Degradation by *Salmonella* under Phagosome-Mimicking Culture Conditions Investigated using Comparative Peptidomics"; Molecular & Cellular Proteomics 6.4; Jan. 16, 2007; pp. 717-727.

Nandakumar, R., et al.; "Proteomic Analysis of Endodontic Infections by Liquid Chromatography-Tandem Mass Spectrometry"; Oral Microbiology Immunology, vol. 24; Feb. 2009; pp. 347-352.

Hernychova, Lenka, et al.; "Detection and Identification of Coxiella burnetii Based on the Mass Spectrometric Analyses of the Extracted Proteins"; Analytical Chemistry, vol. 80, No. 18; Sep. 15, 2008; pp. 7097-7104.

Pratt, Julie, et al.; "Multiplexed Absolute Quantification for Proteomics using Concatenated Signature Peptides Encoded by QconCAT Genes"; Nature Protocols, vol. 1, No. 2; Feb. 2006; 17 pages.

Brun, Virginie, et al.; "Isotope-Labeled Protein Standards"; Molecular & Cellular Proteomics 6.12; Sep. 11, 2007; pp. 2139-2149.

López-Ferrer, Daniel, et al.; "On-Line Digestion System for Protein Characterization and Proteome Analysis"; Analytical Chemistry, vol. 80, No. 23; Dec. 1, 2008; pp. 8930-8936.

López-Ferrer, D., et al.; "Ultra Fast Trypsin Digestion of Proteins by High Intensity Focused Ultrasound"; Journal of Proteome Research, vol. 4; Aug. 12, 2005; pp. 1569-1574.

Gaskell, Simon J.; "Electrospray: Principles and Practice"; Journal of Mass Spectrometry, vol. 32; Jul. 1997; pp. 677-688.

Anderson, Leigh, et al.; "Quantitative Mass Spectrometric Multiple Reaction Monitoring Assays for Major Plasma Proteins"; Molecular & Cellular Proteomics 5.4; Dec. 6, 2005; pp. 573-588.

Han, Bomie, et al.; "Proteomics: From Hypothesis to Quantitative Assay on a Single Platform. Guidelines for Developing MRM Assays using Ion Trap Mass Spectrometers"; Briefings in Functional Genomics and Proteomics, vol. 7, No. 5; Jun. 25, 2008; pp. 340-354.

Wang, Kai-Yi, et al.; "Multiplexed Immunoassay: Quantitation and Profiling of Serum Biomarkers using Magnetic Nanoprobes and MALDI-TOF MS"; Analytical Chemistry, vol. 80, No. 16; Aug. 15, 2008; pp. 6159-6167.

Bundy, Jonathan, et al.; "Lectin-Based Affinity Capture for MALDI-MS Analysis of Bacteria"; Analytical Chemistry, vol. 71, No. 7; Apr. 1, 1999; pp. 1460-1463.

Ho, Kun-Chan, et al.; "Using Biofunctionalized Nanoparticles to Probe Pathogenic Bacteria"; Analytical Chemistry, vol. 76, No. 24; Dec. 15, 2004; pp. 7162-7168.

Lin, Ya-Shiuan, et al.; "Affinity Capture using Vancomycin-Bound Magnetic Nanoparticles for the MALDI-MS Analysis of Bacteria"; Analytical Chemistry, vol. 77, No. 6; Mar. 15, 2005; pp. 1753-1760.

Seng, Piseth, et al.; "Ongoing Revolution in Bacteriology: Routine Identification of Bacteria by Matrix-Assisted Laser Desorption Ionization Time-of-Flight Mass Spectrometry"; Clinical Infectious Diseases, vol. 49; Jul. 7, 2009; pp. 543-551.

Lopez-Ferrer, Daniel, et al.; "Chapter 8: Ultra-Fast Sample Preparation for High-Throughput Proteomics"; Sample Preparation in Biological Mass Spectrometry; May 20, 2011; pp. 125-139.

Duan, Chaojun, et al.; "Chapter 11: Preparation Technology of Protein Samples"; Experimental Technology of Molecular Biology and Proteomics; Dec. 31, 2010; pp. 128-140.

Salvi, G. et al., "Effective Interactions Between Chaotropic Agents and Proteins" Proteins: Structure, Function, and Bioinformatics, vol. 61, 2005, pp. 492-499.

Hielscher, "Ultrasonic Lysis: Cell Disruption & Extraction," copyright 1999-2018, retrieved from: <https://www.hielscher.com/ultrasonic-lysis-cell-disruption-extraction .htm 6 pgs>.

The Free Dictionary, "Conjointly," Retrieved from: <https://www.thefreedictionary.com/conjointly> copyright 2016, 2 pgs.

Janecki, D.J., et al., "Denaturation of metalloproteins with EDTA to facilitate enzymatic digestion and mass fingerprinting," Rapid Communications in Mass Spectrometry, vol. 19, 2005, pp. 1268-1272.

Martinez-Maqueda, D., et al., "Extraction/ Fractionation Techniques for Proteins and Peptides and Protein Digestion," Proteomics in Foods: Principles and Applications, F. Toldra and L.M.L. Nollet (Eds.) Springer, Chapter 2, 2012, 32 Pages.

Gundry, R.L., et al., "Preparation of Proteins and Peptides for Mass Spectrometry Analysis in a Bottom-Up Proteomics Workflow," Current Protocols in Molecular Biology, Unit 10.25, Oct. 2009, pp. 1-29.

METHOD FOR OBTAINING PEPTIDES

CROSS-REFERENCE TO RELATED APPLICATIONS

This application is a continuation of U.S. patent application Ser. No. 14/398,339, filed on Oct. 31, 2014. U.S. patent application Ser. No. 14/398,339 claims priority to PCT/EP2013/059192 filed on May 2, 2013, which claims priority to FR1254090 filed May 3, 2012. U.S. patent application Ser. No. 14/398,339, Application No. PCT/EP2013/059192, and Application No. FR1254090 are incorporated herein by reference in their entirety.

TECHNICAL FIELD

The present invention relates to a method of obtaining peptides from procaryotic and/or eucaryotic cells for their subsequent analysis.

The analysis of these peptides can indeed prove useful in a large number of applications, particularly in biomarker research or bacterial peptide analysis, for example within the framework of applications of identification, typing, detection of resistance and virulence markers, and this within the medical, pharmaceutical and agro-food fields.

STATE OF THE ART

The protocols of extraction and purification of peptides according to the prior art are generally very lengthy. Moreover, these methods are, generally, manual and complex to implement.

International application WO 2006/031063 describes compositions intended to hydrolyse polypeptides, this hydrolysis reaction being obtained chemically by the use of a solution called "PCA", comprising an acid (such as pure acetic acid), a water-miscible organic solvent (such as acetonitrile) and a reducing agent (such as tris(2-carboxyethyl)phosphine). This chemical digestion is performed at 99.9° C. for two hours. However WO 2006/031063 makes provision, optionally, for linking this step of chemical digestion to a prior step of enzymatic digestion, possibly in order to increase the efficiency of the proteolysis. The enzymatic digestion step is performed at 37° C. for 12 hours using a modified trypsin, subsequently to a thermal denaturation step (90° C. for 20 minutes). The above-mentioned step of chemical digestion is performed following this step of enzymatic digestion (99.9° C. for 2 hours). The total treatment time of the protein sample is therefore greater than 14 hours, which represents an indisputable major disadvantage. Moreover, WO 2006/031063 teaches the use of a modified trypsin, more expensive than a conventional trypsin.

International application WO 2008/128029, for its part, discloses a method of protein or peptide fragmentation in solution, said method comprising, subsequently to the initial step of enzymatic or chemical digestion, a series of additional steps of separation and fragmentation. The latter contribute on the one hand to increasing the time of the fractionation method overall and, on the other, require various manipulations, thus rendering the automation of this method extremely difficult.

U.S. Pat. No. 7,622,273 describes a protocol intended to denature the post-translationally modified polypeptides or proteins, these peptides and proteins being directly bound to a protein microarray and said protocol comprising the steps of chemical treatment, enzymatic or chemical digestion and of subsequent identification of proteins on said protein microarrays. The step of chemical treatment comprises the denaturation, the reduction and the alkylation of said proteins, while that of enzymatic digestion includes the deglycosylation and/or dephosphorylation of said proteins and the digestion of the latter by chemical or enzymatic proteolysis. All the reactions are performed sequentially on protein microarray. The step of chemical treatment lasts at least 3 hours and 15 minutes and that of enzymatic digestion two hours (cf. Example 1), i.e. a minimum duration of 5 hours and 15 minutes. This, although less than the duration of the conventional methods—approximately 24 hours—nevertheless remains unsatisfactory, particularly having regard to the requirements inherent in the clinical or pharmaceutical fields. What is more, the complex samples (plasma, urine, cerebrospinal fluid, etc.) can require fractionation or depletion strategies to isolate the target proteins prior to the implementation of the protocol disclosed in this patent, which increases the total treatment duration of said samples accordingly. International application WO 2011/130521 describes a method of proteolytic digestion, which uses a range of pressure cycles (for example from 5 to 35 kpsi, i.e. approximately from 344.74 bars to 2413.16 bars) in order to reduce the duration of this method. Even if this duration seems shorter than the methods of the prior art, it nonetheless remains that the cumulated time corresponding to the steps of reduction (10 mM of DTT at 37° C. for 1 hour) and of alkylation (50 mM of iodoacetamide at ambient temperature, in darkness, for 45 minutes) cannot be less than 1 hour and 45 minutes. If to this is added the time of lysis of the microorganisms (3 minutes at 4500 rpm), the time of manipulation of the lysate before the step of reduction (not specified) and that inherent in the dilutions of the solution before the step of enzymatic digestion under pressure (also not specified), it is obvious that the total duration of the protocol which is the object of WO 2011/130521 cannot be less than 2 hours, which remains unsatisfactory. Due to the high pressures used, this method requires a complex apparatus, able to withstand these high pressures, difficult to operate and expensive. What is more, said method requires additional steps of filtration in order to reduce the very high concentrations of chaotropic agent (8M urea), prior to the step of enzymatic digestion in order not to risk inactivation of the enzyme used Indeed, when used at high concentration (from 1M), the chaotropic agents used at the step of denaturation of the proteins—such as urea—will also denature the protein structure of the enzyme(s) used at the step of enzymatic proteolysis and will have the consequence of totally or partially inactivating this enzyme. In order to prevent this, it is necessary, before the step of enzymatic proteolysis (enzymatic digestion), to perform additional steps of dilution and/or of filtration, which requires an additional time lapse and makes the automation of the method as a whole more complex. An alternative consists in using genetically modified enzymes (for example modified trypsins) capable of performing protein digestion in the presence of high concentrations of chaotropic agent(s). However, these modified enzymes have less rapid action kinetics than those of the native enzymes and have a much higher purchase cost than these latter.

There therefore exists a need to develop a protocol permitting for obtaining of peptides from procaryotic and/or eucaryotic cells which resolves all or part of the above-mentioned problems, i.e. an efficient, rapid, easily automatable protocol not requiring unnecessary steps of dilution.

DISCLOSURE OF THE INVENTION

Thus an object of the present invention relates to a method of obtaining peptides from procaryotic and/or eucaryotic cells, said method comprising the following steps:

a) lysis of the procaryotic and/or eucaryotic cells and recovery of the proteins thus obtained,
b) denaturation of said proteins using at least one denaturing agent,
c) alkylation of the denatured proteins using at least one alkylating agent,
d) enzymatic proteolysis of the proteins obtained at the end of step c) using at least one proteolytic enzyme,
e) recovery of the peptides obtained at the end of the step of enzymatic proteolysis d), in which the lysis of the procaryotic and/or eucaryotic cells in step a) is lysis at a low concentration of chaotropic agent(s).

This method (protocol) of obtaining peptides is applicable to procaryotic cells (for example to bacteria), to eucaryotic cells (human, animal, yeast, etc. cells) or to a mixture of procaryotic and eucaryotic cells.

According to a preferred embodiment, the method according to the present invention will be used in order to obtain peptides from procaryotic cells, preferably from bacteria (Gram+ or Gram−).

By "denaturing agent" is understood an agent—physical or chemical—capable of inducing a phenomenon of denaturation of proteins and polypeptides; the latter leaving their native state and little by little losing their secondary, tertiary and quaternary structure. The denaturation can sometimes be reversible, the return to the native state then being possible and the activity of the protein being restored.

The denaturation of the proteins is due to the sensitivity of the latter depending on their physico-chemical environment. The proteins are denatured when the interactions between the residues are disrupted by a denaturing agent. The covalent bonds between adjacent amino acids of the polypeptide chain are not broken. Conversely, certain conditions of denaturation can cause the breaking of disulphide bonds between non-adjacent cysteine residues of the polypeptide chain which provide the overall stability of the quaternary structure of the protein.

As denaturing agent are principally distinguished:
a) physical agents, such as temperature; the increase of the temperature indeed causes thermal agitation of the atoms of the molecule; this causes breakage of weak interactions like the hydrogen bonds, which stabilise the spatial structure;
b) chemical agents, such as:
  acids and bases; by modifying the surrounding pH they induce a modification of the charges carried by the ionisable groups and therefore damage the ionic and hydrogen bonds stabilising the spatial structure of the protein;
  chaotropic agents such as urea, guanidine salts (for example guanidine hydrochloride or lithium perchlorate); used at high concentrations, these compounds greatly weaken the hydrogen bonds of the proteins (main low-energy bonds responsible for maintaining the secondary, tertiary and quaternary structures of the proteins);
  thiol reducing agents such as 2-mercaptoethanol or dithiothreitol (DTT); they permit cleaving of the disulphide bridges and thus contribute to weakening the tertiary or quaternary structure of the proteins;—detergents, which act by modification of the interaction with the aqueous solvent (for example sodium dodecyl sulphate—better known under the acronym "SDS").

Certain denaturing agents can prove non-reversible, such as the heavy metals (Pb, Hg, etc.) and certain acids (for example $HNO_3$, trichloroacetic acid, etc.

Of the chaotropic agents, a distinction is made, for the purposes of the present invention, between so-called "saline" chaotropic agents, such as the salts of guanidine (or of guanidinium) and so-called "non-saline" chaotropic agents, such as urea.

By "lysis at low concentration of "chaotropic agent(s)", is understood lysis at a concentration of chaotropic agent(s) less than or equal to 1M, preferably less than or equal to 100 mM.

Indeed, at such concentrations, so-called "chaotropic" agents no longer exercise denaturing activity on proteins and polypeptides, thus losing their chaotropic property.

This technical solution is in contrast to the conventional solutions presented in the prior art, which generally employ chaotropic agents and more particularly guanidine salts (such as guanidine hydrochloride, guanidine thiocyanate, etc.)—at generally very high concentrations, of the order of 6M. Such concentrations of chaotropic agents—and particularly of salts (for example of guanidine salts)—greatly interfere with the enzymatic proteolysis, in particular when the latter is performed using a serine protease such as trypsin. The fact, within the framework of the method of obtaining peptides according to the present invention, of performing lysis at a low concentration of chaotropic agent(s) not only permits improvement of the efficiency of the proteolysis step d) but also prevents having to have recourse to additional filtration/dilution steps before said proteolysis step. The time saving achieved allows a significantly more rapid protocol to be obtained than those described in the state of the art, but which is also more easily automatable.

Moreover, this low concentration of chaotropic agent(s) allows the use of native proteolytic enzymes and does not require recourse to genetically modified proteolytic enzymes, which have less rapid action kinetics than those of the native enzymes and have a much higher purchase cost than the purchase cost of the latter.

According to a preferred embodiment, lysis is effected at a low concentration of salt(s), which means that the lysis is performed at a salt concentration less than or equal to 50 mM, preferably less than or equal to 30 mM.

Advantageously, the lysis at low concentration of chaotropic agent(s) is performed in the absence of non-saline chaotropic agent(s) such as urea. Indeed, the method according to the present invention does not require the use of such non-saline chaotropic agents.

For lysis at a low concentration of chaotropic agent(s), it is preferable to use the universal protocol of cellular lysis of procaryotes and/or eucaryotes described in international application WO 02/10333 the whole of the content of which is incorporated by reference in the present patent application. This universal protocol consists in a method of cellular lysis of procaryotes and/or of eucaryotes or of simultaneous cellular lysis of procaryotes and eucaryotes which consists in adjusting at least three of the following parameters:
  a percentage by mass of active beads (lysing beads) of small diameter relative to active beads (lysing beads) of large diameter less than or equal to 50%, and/or
  a total mass of lysing (active) beads comprising a mixture or otherwise of beads of small diameter and/or of beads of large diameter, of between 50 and 100% relative to the total mass of the biological sample treated, and/or
  a duration of lysis of between 10 and 20 min, and/or
  a number of non-lysing glass beads for driving lysing (active) beads less than seven (7), and/or—a number of non-lysing iron beads for driving lysing (active) beads of between five (5) and fifteen (15), depending on the technique used:

sonication,
mechanical vortex, or
magnetic vortex.

Preferably, the lysing (active) beads of small diameter are of a diameter of between 90 and 150 µm and preferably approximately 100 µm, and the lysing (active) beads of large diameter are of a diameter of between 400 and 600 µm and preferably approximately 500 µm.

Still preferably, the lysing (active) beads are made of glass.

According to a preferred embodiment, still such as indicated in application WO 02/10333, if the mechanical vortex technique is used, the method consists in performing the lysis according to the following parameters:
  a duration of lysis of 11 to 20 min, preferably of 15 to 20 min and still more preferably of 20 min,
  a percentage of 100 µm diameter beads of less than 50%, preferably less than 30%, and still more preferably of 20%,
  a total mass of lysing (active) beads of greater than 60%, preferably greater than 80%, and still more preferably of 100% of the total mass of the biological sample treated, and
  a number of glass beads less than seven (7) preferably equal to one (1).

If the magnetic vortex technique is used, the method consists, preferably, in performing lysis according to the following parameters:
  a duration of lysis of 12 to 20 min, preferably of 15 to 20 min and still more preferably of 20 min,
  a total mass of lysing (active) beads of 100 µm greater than 80% and preferably of 100% of the total mass of the biological sample treated, and
  a number of iron beads of between five (5) to fifteen (15) beads, preferably of ten (10) iron beads.

Generally, for the purposes of the present invention, any lysis techniques are used with a low concentration of chaotropic agent(s) not requiring recourse to high pressures of the order of several hundreds or even thousands of bars. Indeed, one of the objectives of the present invention is the elaboration of a protocol for obtaining peptides which is efficient, rapid and can be implemented by means of a standard apparatus, without requiring the use of a specifically adapted apparatus to withstand high or even very high pressures, an apparatus which is complex to employ and extremely costly.

The method of obtaining peptides according to the present invention is implemented at a pressure of from atmospheric pressure to a pressure of approximately one hundred bars. Preferably, said method is implemented under a pressure of 100 bars, preferably less than 50 bars, advantageously less than 10 bars. According to a preferred embodiment, the method according to the present invention is performed at atmospheric pressure.

According to a preferred embodiment of the present invention, the lysis at a low concentration of chaotropic agent(s) is lysis by sonication effected by means of an ultrasound probe. Preferably this lysis by sonication is effected by means of said ultrasound probe in the presence of a mixture of glass beads of 1000 µm and of zirconium beads of 100 µM.

Within the framework of lysis by sonication, preferably, the protocol is applied for lysis by sonication such as described in international application WO 02/10333 (p. 3, l. 18-26), i.e. using the following parameters:
  a duration of lysis of 9 to 20 min, preferably of 12 to 18 min and still more preferably of 15 min,
  a percentage of beads of 100 µm diameter of between 10 to 50% preferably of between 20 and 30% and still more preferably of 20%, and
  a total mass of lysing (active) beads of between 50 to 100% of the total mass of the biological sample treated, preferably of between 75 and 90% and preferably between 80 and 85%.

Concerning the apparatus and methodology of the protocol for lysis by sonication per se, in advantageous manner, an external sonotrode such as the VialTweeter sonotrode marketed by the company Hielscher is used. Such a probe consists in a vibrating block drilled with holes in which can be inserted vials such as Eppendorf vials of 1.5 ml volume into which are introduced the cells to be lysed in suspension in a 3 mM Borate pH 8 buffer as well as the 1 mm glass and 100 µm zirconium beads (50 mg of each). The vial is closed and then the sonotrode activated for 5 to 15 minutes, preferably 10 minutes, at an amplitude of between 50% and 100% of the nominal amplitude (between 5 and 10 watts for each vial depending on its position in the block), preferably 100% and a cyclic ratio of 40% to 60%, preferably of 50%.

The selection of a protocol for lysis by sonication is not in any case and arbitrary choice. Much to the contrary, the applicant has, in surprising manner, discovered that the yield of the method of obtaining peptides according to the present invention is better when the step of lysis a) was a step of lysis by sonication.

Moreover, the applicant has discovered that the omission of the step of preheating the ultrasound probe (activation of the probe lasting 1 h, which raises the temperature of the whole of the vibrating system to 95° C.) did not impair the efficiency of said method. This proves to be an altogether advantageous characteristic in that this step of preheating of the ultrasound probe reduces its lifetime and requires an additional contribution of energy.

In consequence of which, in preferred manner, the ultrasound probe is not subjected to a step of preheating prior to lysis by sonication.

Regarding the step of enzymatic proteolysis d), this latter is performed by action of a proteolytic enzyme, preferably a serine protease, advantageously selected from the group consisting in trypsin, chymotrypsin and elastase. Preferably, said proteolytic enzyme is trypsin.

This enzymatic proteolysis is particularly preferred relative to the physico-chemical treatments (treatments with hydrogen peroxide, cyanogen bromide, trifluoroacetic acid, etc.) as it preserves the structure of the proteins more, proves easier to control and cleaves the peptide chains at specific sites (at the C-terminal of lysine and arginine residues in the case of trypsin). By "enzymatic proteolysis" is understood the single or combined action of one or more enzymes under appropriate reaction conditions. The enzymes performing the proteolysis, called proteases, cleave the proteins in site-specific manner. Indeed each protease generally recognises a specific sequence of amino acids in which this protease always performs the same cleavage. Certain proteases recognise a single amino acid or a sequence of two amino acids between which they perform a cleavage, other proteases recognise longer sequences of amino acids. These proteases can be endoproteases or exoproteases. Among these known proteases can be cited, as described in the document WO 2005/098071:
  specific enzymes such as trypsin which splits the peptide bond at the carboxylic group of the Arg and Lys residues, endolysin which cleaves the peptide bond of the —CO group of the lysines, chymotrypsin which hydrolyses the peptide bond at the carboxyl group of the aromatic residues (Phe, Tyr and Trp), pepsin which cuts at the NH2 group of the aromatic residues (Phe, Tyr and Trp), V8 protease of the V8 strain of *Staphylococcus aureus* which cleaves the peptide bond at the carboxyl group of the Glu residue;

non-specific enzymes such as thermolysin derived from the bacterium *Bacillus thermoproteolyticus* which hydrolyses the peptide bond of the NH2 group of the hydrophobic amino acids (Xaa-Leu, Xaa-Ile, Xaa-Phe), subtilisin and pronase which are bacterial proteases which hydrolyse practically all the bonds and can transform proteins into oligopeptides under controlled reaction conditions (enzyme concentration and reaction duration).

Several proteases can be used in a simultaneous manner, if their modes of action are compatible, or they can be used successively. Within the framework of the invention, the digestion of the sample is, preferably, performed by action of a protease enzyme having good cleavage site selectivity, for example trypsin.

The obtaining of peptides by means of a chemical reagent or of a protease can be obtained by simple reaction in solution. It can also be implemented with a microwave oven or under pressure or with an ultrasound device In these three last cases, the protocol can be much more rapid.

Of the peptides obtained by enzymatic digestion (enzymatic proteolysis), the specific peptides of the protein are called proteotypic peptides. The latter are easily detected by mass spectrometry or other appropriate analytical techniques suited to the detection of such proteotypic peptides. This represents an additional advantage relative to chemical proteolysis, obtained by means of physico-chemical treatments.

Preferably, the denaturing agent is a thiol reducing agent, preferably selected from 2-mercaptoethanol, tris(2-carboxyethyl)phosphine (TCEP), dithioerythritol (DTE), tributylphosphine and dithiothreitol (DTT), advantageously said thiol reducing agent is tris(2-carboxyethyl)phosphine or dithiothreitol.

Preferably, the alkylating agent is selected from the group formed by N-ethylmaleimide, iodoacetamide and M-biotin, preferably said alkylating agent is iodoacetamide (IAA).

Using the parameters of the method according to the present invention, the minimum duration of the enzymatic proteolysis step d), until now a limiting factor, is drastically reduced. Indeed, the minimum duration of this enzymatic proteolysis step within the framework of the method of obtaining peptides according to the present invention is approximately 15 minutes (preferably this minimum duration is 5 minutes). The reduction of the minimum duration required to obtain the peptides at the end of the enzymatic proteolysis step allows reduction, very significantly, of the total duration of the method of obtaining peptides according to the present invention, since the latter can be performed in approximately barely a half-hour.

Generally, the total duration of the method of obtaining peptides according to the invention is less than 1 hour and 45 minutes, preferably less than 1 hour, advantageously less than 45 minutes and, optimally, approximately 30 minutes.

The significant time saving thus obtained is altogether important particularly with regard to the requirements inherent in the clinical and/or pharmaceutical fields. Moreover, the method of obtaining peptides according to the present invention is perfectly suited to complex samples (plasma, urine, cerebrospinal fluid etc.) which are likely to require additional fractionation or depletion strategies, in order to isolate the target proteins prior to implementation of the method of obtaining peptides. Thus, and even including the time necessary for performing such additional fractionation and depletion strategies, the treatment time of such complex samples by application of the method according to the invention remains very advantageous in comparison with the methods of the prior art.

The prior purification treatment of procaryotic and/or eucaryotic cell samples, before the lysis step a) is known to the man skilled in the art and can in particular implement techniques of centrifugation, filtration, electrophoresis or chromatography. These separative techniques can be used alone or combined with each other to obtain multidimensional separation. For example, multidimensional chromatography can be used by associating separation by ion-exchange chromatography with reverse-phase chromatography, as described by T. Fortin et al. or H. Keshishian et al. In these publications, the chromatographic medium can be in column or in cartridge (solid-phase extraction). The electrophoretic or chromatographic fraction (or the retention time in mono or multidimensional chromatography) of the proteotypic peptides is characteristic of each peptide and the implementation of these techniques therefore permits selection of the proteotypic peptide or peptides to be assayed. Such fractionation of the peptides generated allows an increase in the specificity of the subsequent assay by mass spectrometry.

An alternative to the techniques of electrophoresis or of chromatography, for the fractionation of peptides, consists in specifically purifying N-glycopeptides (and patent application WO 2008/066629). Nevertheless, such purification only allows the quantification of the peptides having undergone post-translational modification of N-glycosylation type. Now not all the proteins are glycosylated, which therefore limits its use.

In terms of prior purification treatment of the procaryotic and/or eucaryotic cell samples, the method according to the invention, preferably, comprises, before the step a), the following additional steps:

a') centrifugation of the microorganisms at a rotation speed of between 3500 and 4500 rpm, preferably of the order of 4000 rpm, during a time period of between 4 minutes and 6 minutes, advantageously of 6 minutes, at a temperature of between 15° C. and 25° C., preferably approximately 20° C., a") Elimination of the supernatant and recovery of the pellet containing the microorganisms, a'") Adsorption of said pellet in a solvent.

Advantageously, the solvent used within the framework of the present invention is selected from a solution of acetonitrile and an aqueous solution comprising a pH buffer such as carbonate ions, advantageously said solvent is an aqueous solution comprising carbonate ions, such as a solution of ammonium bicarbonate.

As for the step of prior purification treatment of the above-mentioned sample, the method can comprise, where necessary, subsequently to the step of recovery of the peptides e), steps of concentration of said peptides. By way of example, the step of recovery of the peptides e) can be followed by the following steps:

e1) Centrifugation with a relative centrifugal force of between 13000 g and 15000 g, advantageously approximately 14000 g for a duration of between 25 minutes and 35 minutes, advantageously approximately 30 minutes, at a temperature of between 2° C. and 6° C., advantageously of approximately 4° C., e2) recovery of all or part of the supernatant including the peptides.

According to a first aspect of the present invention, at least the steps of lysis a) and denaturation b) are performed conjointly/simultaneously.

According to a particular embodiment of this first aspect of the invention, steps a) and b) are performed conjointly/simultaneously. Thus, and contrarily to the methods of the prior art, the lysis time is used to denature the proteins. This allows shortening of the duration of the method as a whole and facilitates its automation.

Within the framework of this particular embodiment, the step of alkylation of the denatured proteins c) is performed at a temperature known to the man skilled in the art to be suitable and able to permit the performance of the alkylation treatment of said proteins. This step of alkylation of the proteins c) is preferably performed in the absence of light and at a temperature of between 10° C. and 60° C., preferably between 15° C. and 25° C., advantageously at ambient temperature.

Still within this particular embodiment, the step of enzymatic proteolysis d), for its part, is performed at a suitable temperature, i.e. also known to the man skilled in the art to allow the enzymatic digestion of the proteins (enzymatic proteolysis). Advantageously, this step of proteolysis d) is performed at a temperature of between 30° C. and 60° C., preferably between 37° C. and 55° C., advantageously approximately 50° C.

In this particular embodiment, the duration of the conjoint (simultaneous) steps of lysis a) and of denaturation b) is between 3 minutes and 7 minutes, preferably between 4 minutes and 6 minutes, advantageously said duration is approximately 5 minutes.

Moreover, and still within this particular embodiment, the duration of the step of alkylation of the denatured proteins c) is also of between 3 minutes and 7 minutes, preferably between 4 minutes and 6 minutes, advantageously said duration is approximately 5 minutes.

Still according to this particular embodiment, the method comprises, after the step of alkylation of the denatured proteins c), the following step:
c1) assay of the proteins obtained in said step c),
and in which the proteolytic enzyme is added at the step of enzymatic digestion d) in a ratio by weight (w/w) relative to the weight of the proteins assayed in step c1) of between 1/5 and 1/15, preferably between 1/8 and 1/12, advantageously approximately 1/10.

According to a second aspect of the invention, at least steps a)-c) of the method according to the invention are performed conjointly (a)+b)+c)).

According to a particular embodiment of this second aspect of the invention, steps a)-c) (lysis denaturation and alkylation) are performed conjointly (simultaneously).

According to a third aspect of the present invention—particularly preferred-steps a)-d) are performed conjointly (simultaneously).

According to this third aspect of the present invention—particularly preferred—steps a)-d) of the method according to the present invention are performed conjointly (a)+b)+c)+d)).

More precisely, all the steps a)-d) are performed in a same container (for example an eppendorf vial) without requiring the addition of reagents or manipulation between said steps. This method is therefore easily automatable, which represents a major advantage with a view to cost reduction, limiting risks associated with incorrect manipulation, and reducing the volumes to be used (non-limiting list).

Within the framework of the methods according to the second and third aspects of the present invention, it is necessary to be sure of the compatibility of the agents used in the different steps b), c) and d), and more particularly with regard to the compatibility of the denaturing agent and of the alkylating agent, the latter having a natural tendency to alkylate the denaturing agent introduced in step b).

Preferably, according to these second and third aspects of the invention:
the denaturing agent is a thiol reducing agent selected from tris(2-carboxyethyl)phosphine and dithiothreitol, advantageously said thiol reducing agent is tris(2-carboxyethyl)phosphine, and
the alkylating agent is iodoacetamide. Indeed, the applicant has discovered, in surprising manner, that the use of the TCEP/iodoacetamide (IAA) pair allowed very good yields to be obtained with regard to the method according to the present invention.

A further object of the present invention relates to a method of analysis of peptides of procaryotic and/or eucaryotic cells comprising the following steps:
i) Obtaining peptides from said procaryotic and/or eucaryotic cells using the method according to the invention,
ii) Analysis of the peptides thus obtained, said analysis being performed by means of an analysis of mass spectrometry type.

By way of example, this method of analysis of peptides can be, in the field of microbiology, a method of characterisation of at least one microorganism from a sample, comprising, for example, the identification of said microorganism and the determination of the properties of typing, potential resistance to at least one antimicrobial and virulence factor relating to said microorganism.

A further example relates to biomarker research, particularly from complex biological samples such as plasma, urine, cerebrospinal fluid, etc.

The present invention also relates to a kit for obtaining peptides from procaryotic and/or eucaryotic cells, said kit being specifically suited to the implementation of the method according to the present invention, said kit comprising:
a lysis kit allowing lysis to be performed at low concentration of chaotropic agent(s) of procaryotic and/or eucaryotic cells, preferably a kit for lysis by sonication,
a first solution comprising at least one denaturing agent, preferably selected from 2-mercaptoethanol, tris(2-carboxyethyl)phosphine, dithioerythritol, tributylphosphine and dithiothreitol, advantageously said denaturing agent is tris(2-carboxyethyl) phosphine or dithiothreitol,
a second solution comprising at least one alkylating agent, preferably selected from the group formed of any N-ethylmaleimide, iodoacetamide and M-biotin, preferably said alkylating agent is iodoacetamide,
a third solution comprising at least one proteolytic enzyme such as a serine protease, preferably selected from the group consisting in trypsin, chymotrypsin and elastase, advantageously said proteolytic enzyme is trypsin.

This kit comprises, in optional manner, instructions for use defining its methods of use.

According to a preferred embodiment, said kit comprises:
a kit for lysis by sonication,
a first solution comprising a denaturing agent selected from 2-mercaptoethanol, tris(2-carboxyethyl)phosphine, dithioerythritol, tributylphosphine and dithiothreitol, advantageously said denaturing agent is tris(2-carboxyethyl)phosphine or dithiothreitol, a second solution comprising an alkylating agent consisting in iodoacetamide, a third solution comprising a proteolytic enzyme consisting in trypsin.

Preferably, the lysis kit and the first, second and third solutions are suited and intended to be used conjointly (simultaneously), particularly within the framework of the method according to the third aspect of the present invention, as indicated above.

Yet another object of the present invention relates to the use of a kit according to the invention for implementing the above-mentioned method of obtaining peptides and/or of the method of analysis of peptides also mentioned above.

BRIEF DESCRIPTION OF THE DRAWINGS

The invention, its functionality, its applications and its advantages will be better understood on reading the present description, with reference to the following figures, in which.

DETAILED DESCRIPTION OF THE INVENTION

The examples presented below permit better illustration of the present invention. However, these examples must in no case be seen as limiting the scope of said invention in any manner whatsoever.

Example 1: Protocol P0

Figure 1:
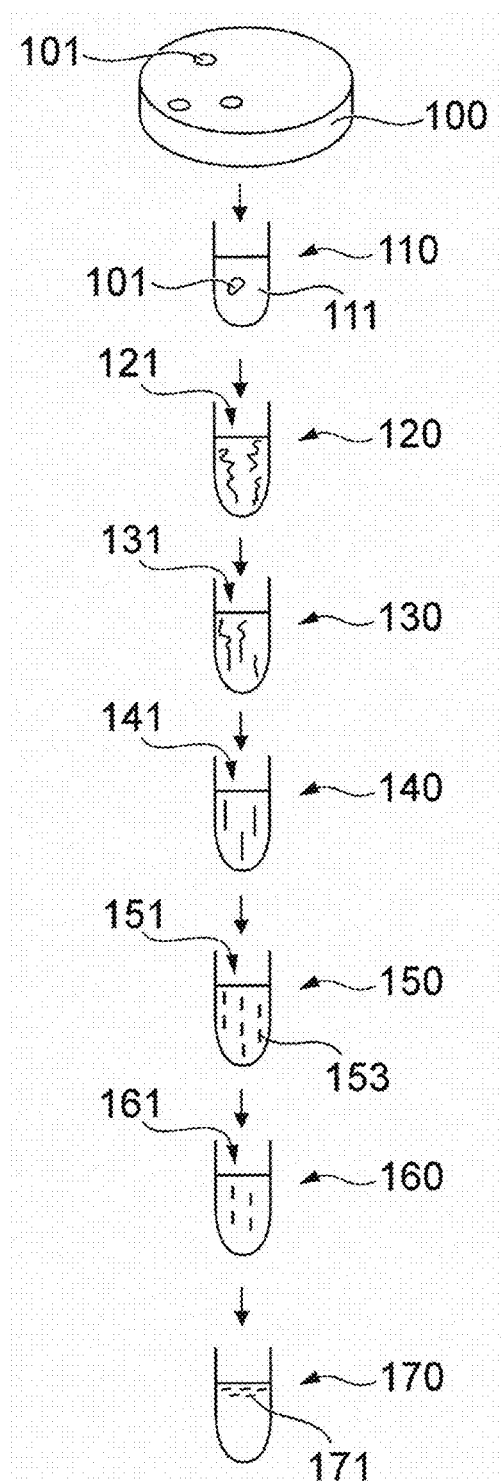
FIG. 1 shows diagrammatically a method of preparation of a sample of microorganisms according to the prior art (P0), this method comprising in particular a step of lysis at high saline concentration (guanidine 6M—chaotropic agent) and a long step of tryptic digestion.

Protocol P0 is a protocol for preparation of a sample conventionally used in the prior art in order to obtain peptides from microorganisms. This method P0 comprises in particular a step of lysis at high salt concentration (guanidine 6M: chaotropic agent) as well as a long step of tryptic digestion. P0 is used below as a reference in order to evaluate the quality/efficiency of the protocols for obtaining peptides according to a first aspect of the invention (protocol P1) Said protocol P0—described below with reference to FIG. 1—lasts for approximately 24 hours and comprises the following steps:

placing in suspension one to three colonies of a microorganism 101 (such as a bacterium of *E. coli* type) cultured on a Petri dish 100 in a vial comprising a solution 111 composed of 100 µl of guanidine hydrochloride 6M, 50 mM Tris-HCl, pH 8, and leaving the lysis reaction 110 to take place for a period of approximately 10 minutes;

introducing, at the denaturation/reduction step 120, a solution 121 comprising 3.5 µl of DTT at a concentration of 150 mM, so as to obtain a final 5 mM solution of DTT; this step of denaturation/reduction being performed in approximately 30 minutes;

then performing the alkylation step 130 by introducing a solution 131 of IAA at a concentration of 150 mM and leaving the alkylation reaction 130 to take place for approximately 45 minutes so as to perform locking (protection) of the thiol functions on the denatured proteins;

prior to the step of tryptic digestion 150, performing a step of dilution 140 by adding 500 µl of a solution 141 comprising 50 mM of $NH_4HCO_3$, in order to diminish the high concentration of chaotropic agent (guanidine 6M) in order not to impair the enzymatic activity of the trypsin at the subsequent step of tryptic digestion 150;

performing this tryptic digestion step 150 by introducing 0.5 to 3 µl of a trypsin solution 151 measured at 1 µg/µL; leaving the enzymatic digestion to take place for 6 to 20 hours (duration allowing the peptides 153 to be obtained);

stopping in step 160 said tryptic digestion 150 by adding 2 µl of formic acid 161; then separating the peptides 171 thus obtained, for example by centrifugation to eliminate the non-soluble species which could hamper the subsequent analytical steps and sampling them in order to perform, where necessary, subsequent steps of analysis (analyses).

Example 2: Protocol P1

Figure 2:
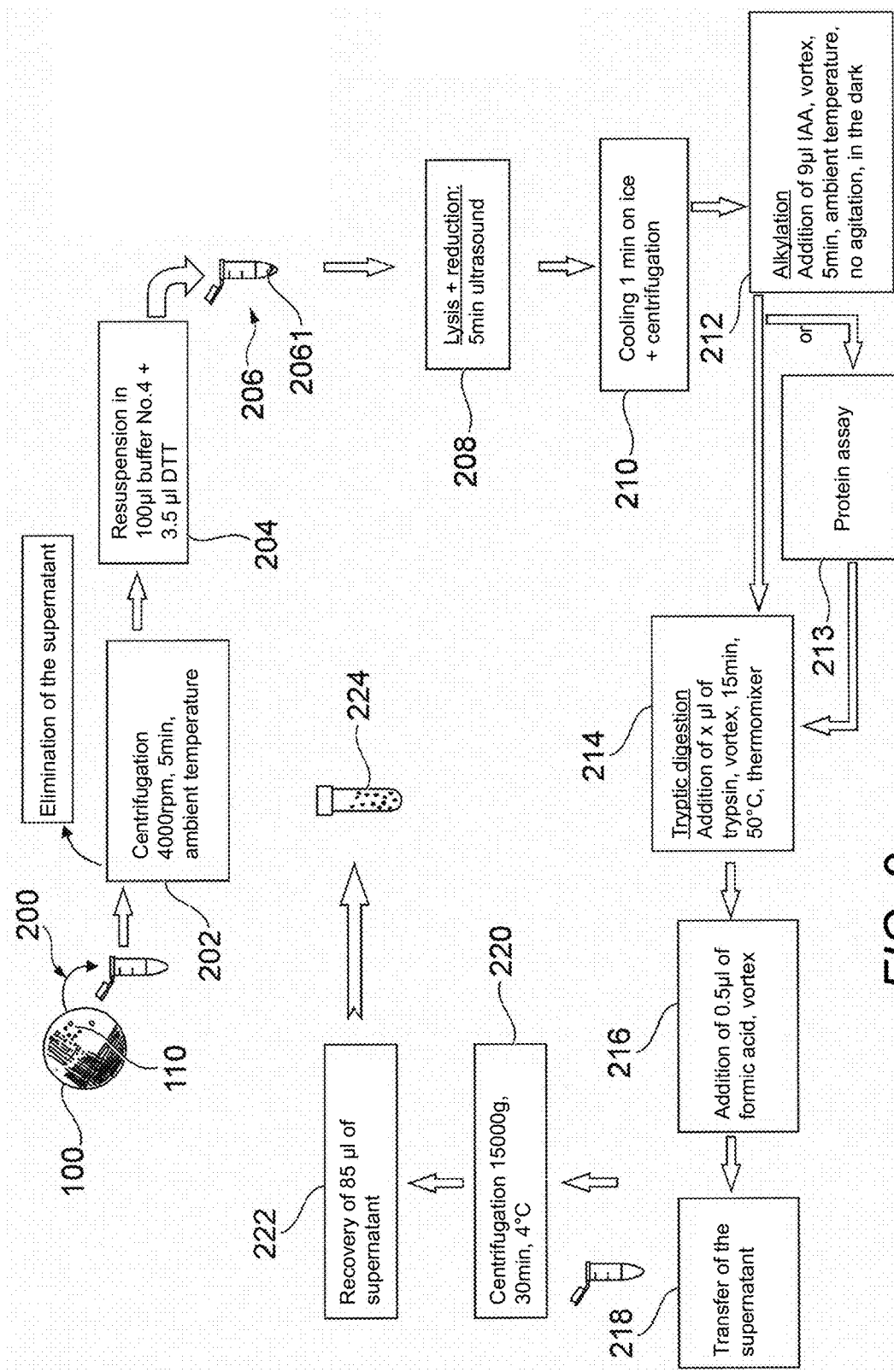
FIG. 2 is a diagram showing the different steps of a method according to a first aspect of the present invention (P1)

A method according to a first aspect of the invention—called "protocol P1" or "method P1"—is described below, with reference to FIG. 2.

This protocol P1 permits very rapid preparation of the sample prior to the subsequent analysis steps, performed, for example, by mass spectrometry. The duration of all of the steps of protocol P1 is approximately 30 minutes. It comprises in particular the following essential steps:

lysis and reduction 208 (performed conjointly/simultaneously), in the presence of DTT 5 min under ultrasound, alkylation 212: in the presence of IAA, 5 min at ambient temperature and without agitation, and enzymatic proteolysis (also called enzymatic digestion) 214: in the presence of trypsin, 15 min at 50° C.

As indicated above, the protocol P1 is performed in approximately 30 minutes and gives similar results (MRM analyses) to those obtained by protocol P0 (cf. Example 1—duration of treatment: 24 h), on each of the three microorganisms assayed, i.e.: *Escherichia coli* ECS (Gram-; hereinafter designated "ECS"), *Staphylococcus epidermidis* SE9 (Gram+; hereinafter designated "SE9") and *Candida albicans* CA16 (yeast; hereinafter designated "CA16").

Equipment and Method
  2.1. Products Used
  BSA/Sigma/reference A9085-5G/lot No.: 097K1513
  Bradford reagent: "Quick Start Bradford Dye Reagent 1X"/Bio-Rad/reference 500-0205/control 210006065
  Formic acid/Fluka/reference: 06450
  Iodoacetamide, (IAA)/Sigma/I6125-5G/lot 099K5300/MM=184.96
  DL-1.4-Dithiothreitol 99%, (DTT)/Acros/165680010/lotA0269816/MM=154.24
  Ammonium bicarbonate/Sigma/A6141-500 g/lot No. 117K0039/MM=79.06
  Ammonium hydroxide, $NH_4OH$/28% ammonia/reference: 21190292/MM=17.03 g
  Trypsin/Promega/reference V511 (storage at −20° C.)
  "Suspension medium" (sterile water) bioMérieux (ref.: 70640)
  *Escherichia coli* strain, ATCC No.: 11775T
  *Staphylococcus epidermidis* strain, ATCC No.: 14990
  *Candida albicans* strain, ATCC No.: 18804
  2.2. Preparation of the Buffer Solutions
  Buffer No. 4: 50 mM ammonium bicarbonate pH8/storage 1 month at +4° C.
  For 50 ml buffer: 197.6 mg of bicarbonate qsp 50 ml $H_2O$/pH=7.9; add approximately 10 μl of $NH_4OH$ to obtain pH=8
  Buffer No. 5: 150 mM DTT/to be prepared extemporaneously
  For 1 ml of buffer: 23.1 mg of DTT qsp 1 ml bicarbonate buffer No. 4
  Buffer No. 6: 150 mM IAA/to be prepared extemporaneously
  For 1 ml buffer: 27.7 mg of IAA qsp 1 ml bicarbonate buffer No. 4
  2.3. Equipment
  Centrifuge "APPLI 24"/Prolabo
  1.5 ml vials "Safe Lock" Eppendorf, ref: 0030120.086
  Centrifuge "benchtop"/Eppendorf/ref 5415C
  Thermomixer "comfort"/Eppendorf
  Microplate reader (595 nm)+microplates+modules
  Spectrophotometer UVIKON+80 μl quartz cuvettes
  Culture dishes BMX: COS (ref.: 43041) and SDA (ref.: 43555)
  Densichek Plus BioMérieux: reference: 21250
  Ultrasound probe "Hielscher"; ref: PN-66-NNN
  Lysis beads 0.1 mm (small diameter): "Zirconia/Silica beads"/Roth/N033.1
  Lysis beads 1 mm (large diameter): "Silibeads typ 1/1.3 mm/ref: 4504/VWR
  Bridges/Dutscher/reference: 011870A
  2.4. Protocol
  2.4.1. Steps 200, 202, 204, 206, 208 and 210

Firstly, the buffer solutions No. 5 (150 mM DTT) and No. 6 (150 mM IAA 150 mM) are prepared.

Using a "spoon" spatula, 50 mg of 0.1 mm diameter beads (small diameter beads) and 50 mg of 1 mm diameter beads (large diameter beads) are weighed and are introduced into the No. 1 vial. The mixture of beads of small diameter and large diameter is represented in FIG. 2 by the numerical reference 2061.

One to three colonies 110 are taken from a Petri dish 100 and are placed in suspension in water in step 200. The concentration of bacteria in the suspension thus obtained is estimated by conventional turbidity measurement methods (measurement of absorption at 550 nm). A volume of suspension corresponding to $1.10^8$ CFU is taken and then centrifuged, in step 202, at 4000 rpm for 5 min, at ambient temperature. At the end of this centrifugation step 202, the pellet is adsorbed (ECS, CA16 and SE9) in step 204 in 100 μl of the No. 4 buffer solution (vial No. 2), then 3.5 μl of 150 mM DTT (buffer No. 5) are added, still in step 204, to obtain a final DTT concentration of 5 mM in vial No. 2. Vortexing is applied for 2 seconds (maximum power) to homogenise the contents of this vial No. 2 and the mixture is pipetted in order to transfer it into vial No. 1, in step 206, containing the mixture of beads of "small diameter" and "large diameter" 2061. Vial No. 2 is eliminated.

A bridge is placed on vial No. 1 to prevent it from opening during lysis by sonication.

Vial No. 1 is then introduced into one of the orifices of the Hielscher Ultrasound probe (the 6 orifices at the end of the probe are supposed to be identical according to the supplier), and then 5 min are timed to perform lysis/reduction 208 (settings Amplitude 100/Cycle 1); the temperature of the mixture, in the vial, reaches approximately 95° C.

Vial No. 1 is removed from the orifice of the probe by means of a "lever" holding the vial by the bridge, then this vial No. 1 is cooled, in step 210, by storing it for 1 minute in ice in order to return the temperature of the mixture in the vial to ambient temperature.

This vial No. 1 is then briefly centrifuged by means of a benchtop centrifuge (at the end of step 210), in order to recover the liquid present in the cap and on the walls.

2.4.2. Alkylation Step 212 (Locking of the Disulphide Bridges of the Proteins by Methylation with IAA)

9 μl of solution of 150 mM IAA (buffer No. 6) are added into vial No. 1 in step 212 to obtain a final molarity of 12.5 mM, said vial No. 1 then being vortexed 2 seconds (maximum power) for homogenisation.

The alkylation reaction 212 is left to take place for 5 min at ambient temperature, in the absence of light.

At this stage, two options are possible, i.e.:
  protocol P1 is followed with the step of tryptic digestion 214 (cf. section 2.4.4. below), using a predefined quantity of trypsin, or
  before this step of tryptic digestion 214 (also called tryptic proteolysis) is performed an assay of the proteins 213 (cf. 2.4.3. below), to be executed in a vial No. 3 which is used only to implement the assay of the proteins 213, in order to evaluate the quantity of trypsin to be added at the step of tryptic digestion 214 as a function of the protein concentration assayed at the end of the alkylation step 212.

2.4.3. Protein Assay 213 (According to the Bradford Method)

The protein assay is performed on the supernatant of the lysate centrifuged for 5 minutes at 14000 rpm. It is therefore necessary, in a first stage, to vortex vial No. 1 (homogenisation of the lysate), and then to pipette the lysate from said vial No. 1 (a part of the 0.1 mm beads is often recovered), to transfer this lysate into a vial (vial No. 3) and to centrifuge this vial No. 3 at 14000 rpm for 5 minutes. The assay is then performed on the supernatant. The vial No. 3 comprising the remaining beads is eliminated.

The quantity of proteins is evaluated as a function of a calibration range of BSA diluted in carbonate buffer and assayed in parallel with the centrifuged lysate (range established from a 1 mg/ml BSA solution and then preparation of 0.1/0.2/0.3/0.4/0.6/0.8 and 1 mg/ml solutions).

The assay is performed on 4 µl of the supernatant of the centrifuged lysate and 4 µl of each of the solutions of the range, in 200 µl of Bradford reagent, on microplate, with the optical density (OD) read at 595 nm.

Figure 3:
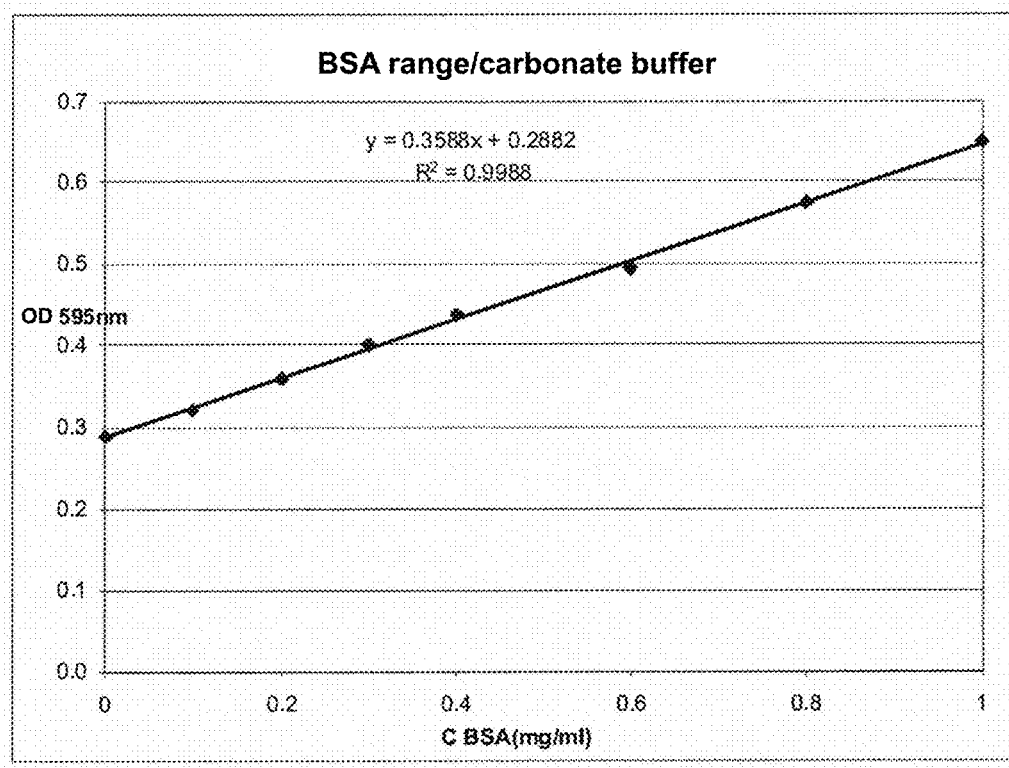
FIG. 3 shows the data relative to the establishment of a calibration range of bovine serum albumin (BSA), thus allowing a correspondence to be obtained between the optical density (OD) measured at 595 nm and the protein concentration (mg/ml), within the framework of said first aspect of the present invention (P1)

An Example of calibration range is shown in FIG. 3.

2.4.4. Tryptic Digestion of the Proteins 214

The thermomixer is preheated, in advance, for 15 minutes at 50° C.

A solution of trypsin adsorbed extemporaneously is used: 20 µg flask of Promega trypsin in 20 µl of the adsorption solution contained in the kit (final concentration 1 µg/µ).

As is known to the man skilled in the art, the maximum activity of trypsin occurs at a pH of 7/9.

If a protein assay has been performed in step 213, the 1 µg/µl trypsin is added in step 214 with a protease/protein ratio by weight (w/w) of 1/10, or 1 µl (=1 µg) for 10 µg of proteins.

Conversely, if such a protein assay 213 has not been performed between the alkylation step 212 and that of tryptic digestion 214, the 1 µg/µl trypsin is introduced into vial No. 1, in step 214, at a standard quantity of 10 µL. Indeed the Applicant has determined that this standard quantity of trypsin allowed satisfactory tryptic digestion to be obtained under all the pertinent conditions of quantities of microorganisms with regard to the desired peptide analysis applications.

Still in step 214, and subsequently to the addition of trypsin, the mixture is vortexed for 2 seconds (maximum power) for homogenisation.

This mixture is then incubated in the thermomixer, 15 minutes at 50° C., 850 rpm.

2.4.5. Stopping the Tryptic Digestion 216

Stopping of the tryptic digestion is effected by an addition of formic acid (qsp pH below 4) in vial No. 1 in step 216. Indeed, trypsin becomes inactive at a pH lower than 4 (this phenomenon is reversible and trypsin becomes active again at a pH greater than or equal to 4).

The pH of the sample was approximately 8 (pH verified with the pH meter/microtube special probe) before addition of 0.5 µl of formic acid. It is approximately 3 after addition of the latter in step 216. The mixture is then vortexed for 2 seconds (maximum power) for homogenisation.

2.4.6. Steps 218, 220, 222 and 224

The peptides resulting from the tryptic digestion are in the supernatant.

The supernatant of vial No. 1 is pipetted (a part of the 0.1 mm beads is often recovered) and transferred into another vial (vial No. 4) in step 218 and then centrifuged, in step 220, for 30 minutes at 15000 g, at a temperature of 4° C.

85 µl of supernatant including the peptides are then recovered in step 222 and introduced into another vial (vial No. 5) in step 224. The latter vial is stored in the freezer at −20° C.

The peptides contained in vial No. 5 are then analysed by MRM in order to determine the quality/efficiency of the protocol P1 (step of validation of the results). The results of these analyses are presented below.

2.5. Validation of the Results

As indicated above, this protocol for obtaining peptides P1 was validated by MRM. The results, for each of the three microorganisms studied (ECS, SE9 and CA 16), respectively, are presented in FIGS. 4, 5 and 6.

Figure 4:
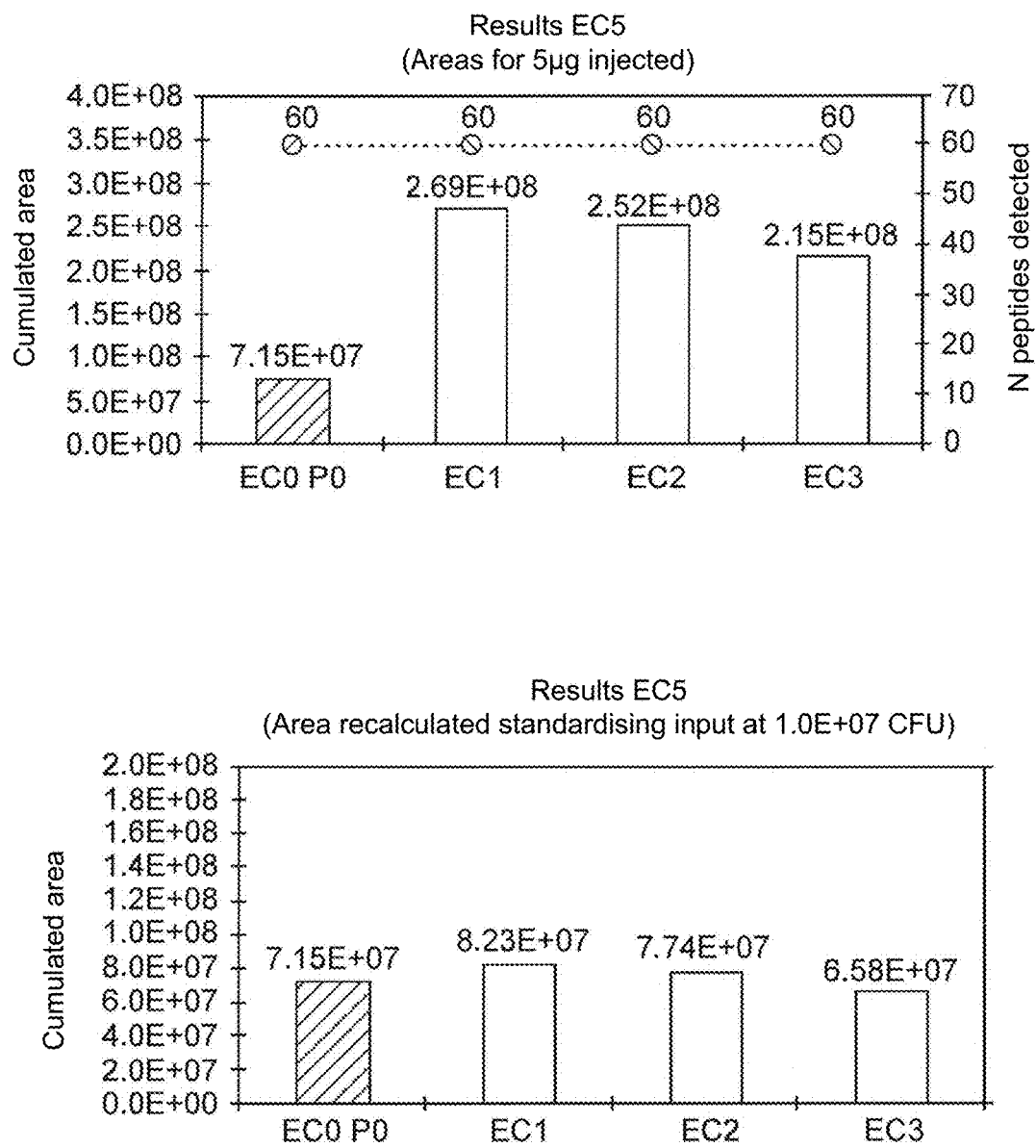
FIGS. 4, 5 and 6 present the results obtained after implementation of the method P1, on each of three microorganisms assayed respectively, i.e. *Escherichia coli* ECS, *Staphylococcus epidermidis* SE9 and *Candida albicans* CA16, FIG. 7 relates to assessment of the possible consequences of the absence of the step of preheating the ultrasound probe within the framework of said method P1.

FIG. 4 shows the results of analysis in MRM mode of peptides obtained with the protocol P1 from $1^e8$ CFU of *E. coli* ECS. The experiment was reproduced three times (columns EC1, EC2, EC3) and compared with the results obtained from the same inoculum using the protocol P0 (hatched bar). The bars represent the sum of the areas under the peaks of the correctly detectable peptides in the mass chromatogram obtained by LC-ESI-MS analysis in MRM mode. This total area represents the intensity of the signals obtained and is linked to the concentration of the corresponding peptides in the analysed solution. The greater this area, the higher is this concentration. The figures also indicate (points connected by lines) the number of correctly detected peptides, out of a possible total of 60 for the analysis settings which have been selected.

The first graph (upper part of FIG. 4) shows the data obtained by standardising the quantity of proteins present in the sample analysed by LC-ESI-MS. The second graph (lower part of FIG. 4) shows the data obtained by modifying the volume of reaction product P1 so as to analyse the equivalent of 1e7 initial CFU. In this case, the comparison of the areas under the peaks permits comparison of the overall yields obtained from the different samples.

In conclusion it appears that:
the method P1 is reproducible for the sum of the accumulated areas under the peaks of the detected peptides, which means that the intensities of these peaks are reproducible overall and suggests that the yields of the different steps of the protocol are reproducible,
this method is equivalent to the reference method P0 (presented in Example 1) in terms of the number of peptides detected with regard to ECS,
this method P1 permits more efficient digestion by trypsin than under the conditions of the protocol P0, as witnessed by the fact that the analysis of equivalent protein masses before digestion results in greater peptide signal intensities for P1 than for P0.
conversely, with an equal quantity of bacteria at the beginning of the protocol, the peptide detection intensities are equivalent for the two protocols, which would seem to suggest that the pre-digestion steps of the protocol P1 are less efficient than in the protocol P0.

Figure 5:
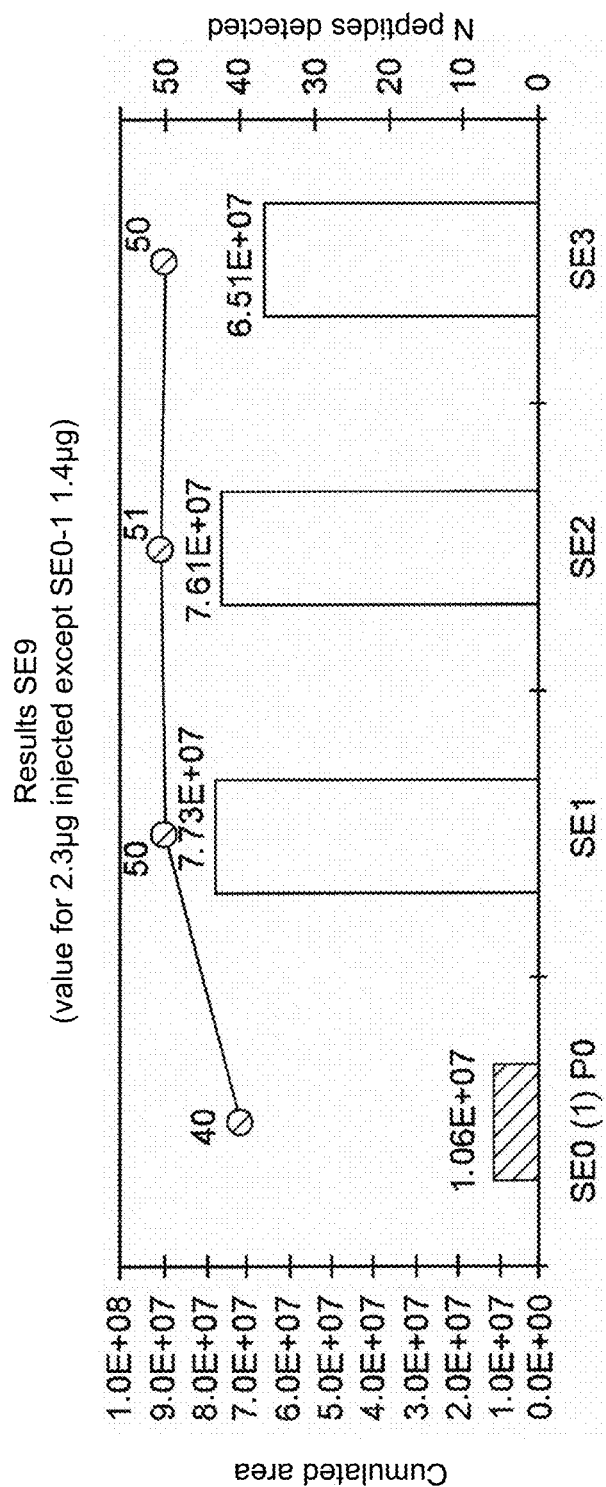

FIG. 5 is the equivalent of the first graph of FIG. 4 (in the upper part) in the case in which the microorganism studied is *S. epidermidis* SE9. According to this FIG. 5, it appears that the conclusions drawn above in the case of *E. coli* ECS are also valid in the case of other species of bacteria—in particular *S. epidermidis* SE9. This is especially true as the equivalent mass of proteins injected is smaller under the P0 conditions than under the P1 conditions.

In conclusion, and despite the fact that the injected quantity is smaller for P0, the method P1 can be regarded as at least equivalent to P0 regarding the detection of peptides of SE9.

Figure 6:
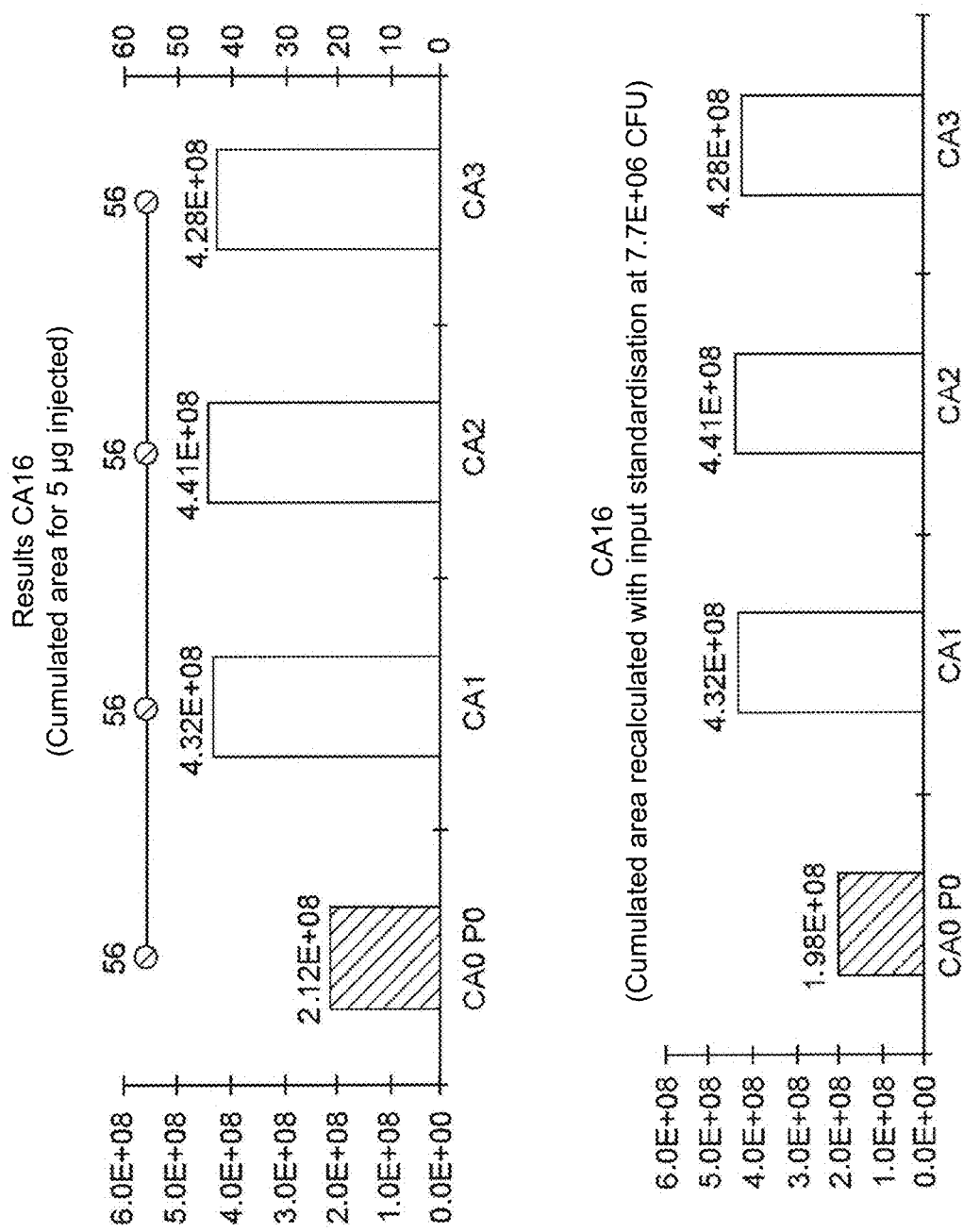

FIG. 6, for its part, shows that regarding the detection of peptides of CA16:
the method P1 is reproducible for the sum of the areas and,
this method is superior to the reference method P0.

2.6. Influence of the Step of Preheating the Ultrasound Probe

The protocol P1 detailed above comprises a step of preheating the "Hielscher" ultrasound probe by allowing this probe to operate "empty" under the conditions then used for the lysis step of the protocol P1 for 1 hour. Under these conditions, the temperature of the vibrating block of the probe is approximately 95° C. This preheating step being susceptible to reducing the lifetime of the ultrasound probe, the applicant has sought to determine the possible consequences of an omission of said step of preheating this ultrasound probe within the framework of the protocol P1. The protocol P1 thus modified is called P1'.

Figure 7:
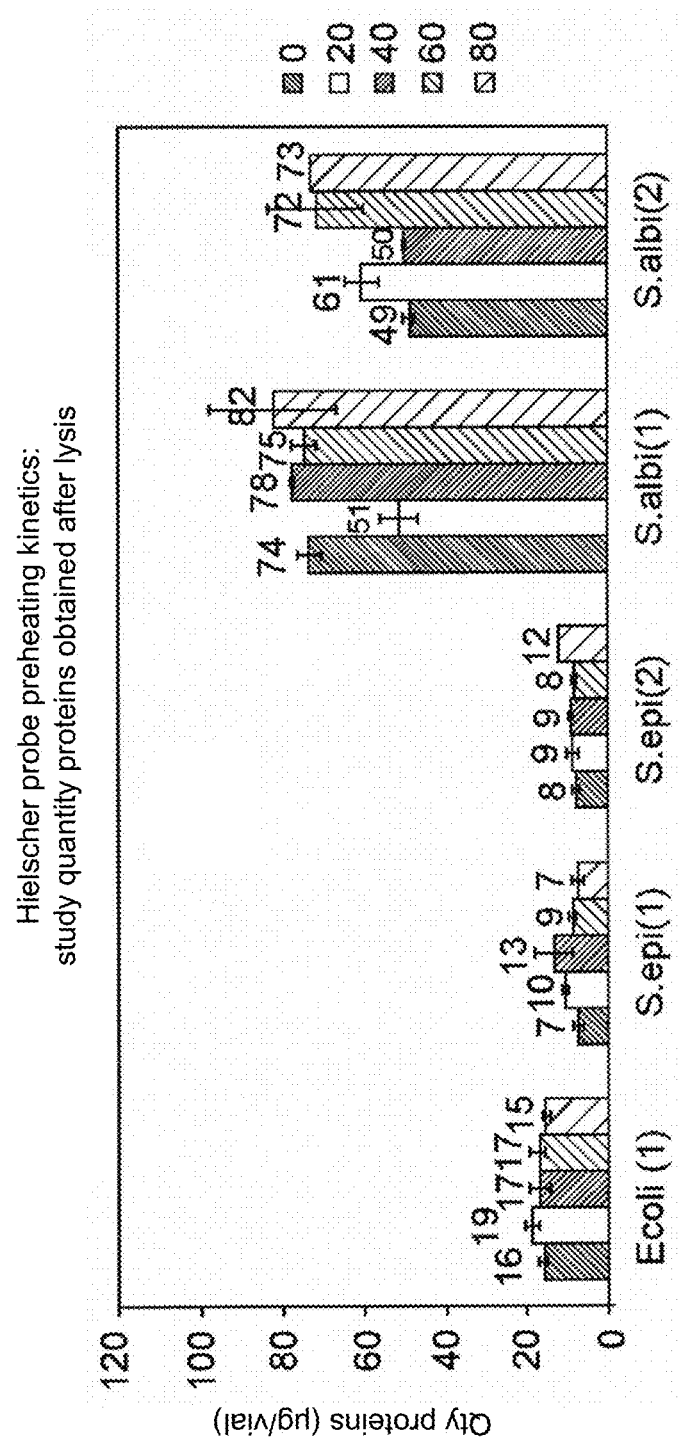

FIG. 7 shows the quantities of assayed proteins after the step of lysis by sonication and reduction 208 (cf. FIG. 2) after different operating times of the sonication probe (0, 20, 40, 60, 80 minutes, the time 0 min corresponding to the use of a probe used after a time of sufficient inactivity for the vibrating block to be at ambient temperature). The protein concentrations have been determined by a Bradford test and are shown on the graphs and expressed in µg for $1^e8$ bacterial cells.

This assay can be conducted by the Bradford method or by any other suitable method known to the man skilled in the art.

The results shown in this FIG. 7 confirm that it is not necessary to preheat the probe before its use to obtain high-quality bacterial lysis.

Moreover, the MRM analyses also confirm that the tryptic digestion trials of the three strains ECS, SE9 and CA16, without preheating of the ultrasound probe used to perform the lysis (protocol P1'), give results superior to the reference protocol P0.

Besides the advantages inherent in the methods for obtaining peptides according to the present invention (cf. above), these methods permit dispensing with the prior step of preheating of the ultrasound probe, within the framework of lysis by sonication. This results in particular in an increased longevity of said ultrasound probe as well as in an energy saving.

Example 3: Protocol P2

Figure 8:
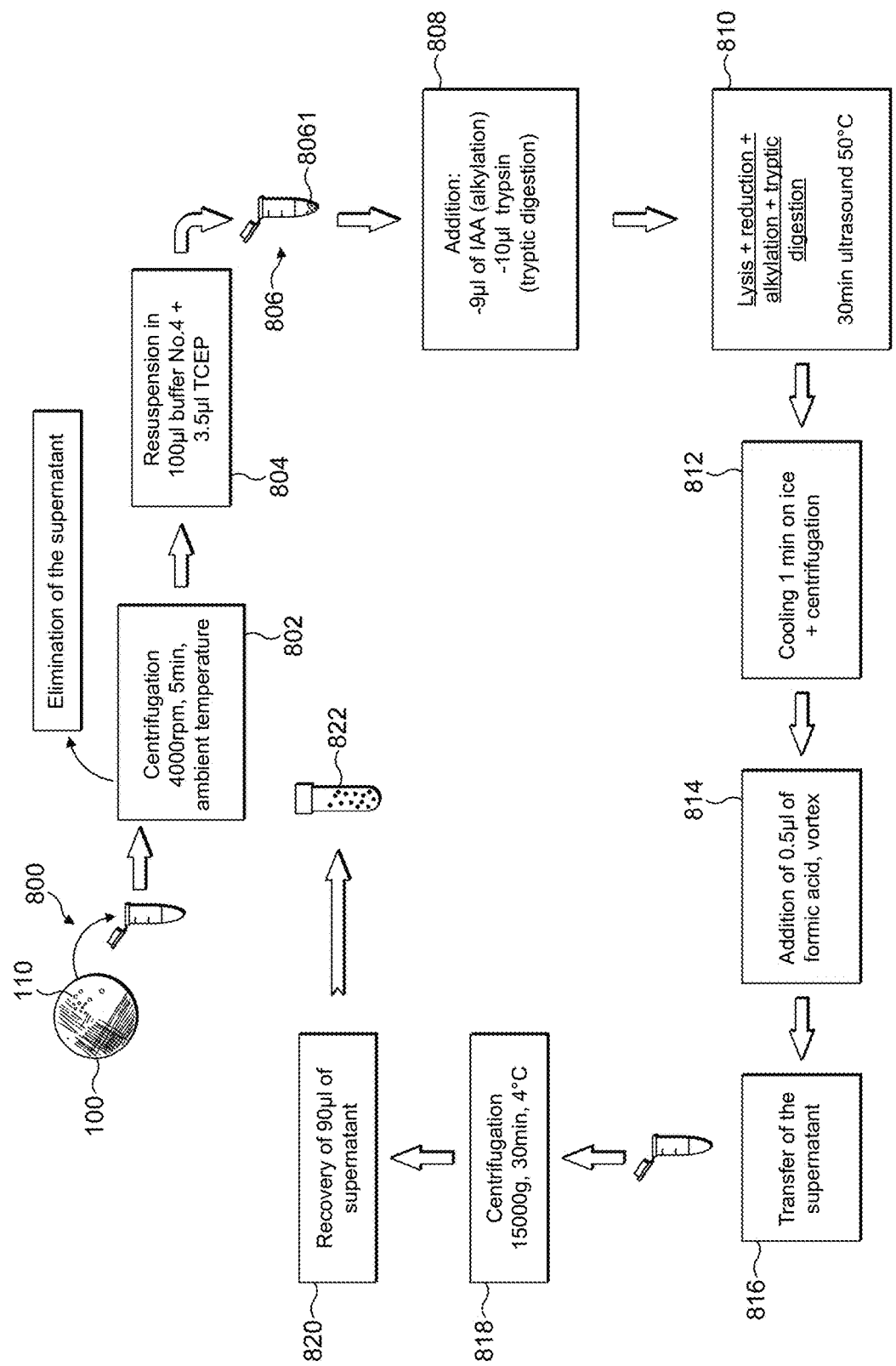
FIG. 8 is a diagram showing the different steps of the method according to a third, particularly advantageous, aspect of the present invention (P2), in which the denaturing agents used is TCEP ("P2-TCEP")

A third aspect of the invention, called "protocol P2" (or "method P2"), is described below, with reference to FIG. 8. This method P2 is particularly preferred within the context of the present invention.

In this Example 3, the method P2 is used to obtain peptides from microorganisms.

This method P2 is a protocol for very rapidly obtaining peptides from procaryotic and/or eucaryotic cells, which can be used in particular prior to steps of analysis by mass spectrometry type.

Just like the protocol P1, this protocol P2 is also performed in approximately 30 min but combines the steps of lysis, denaturation/reduction, alkylation and enzymatic digestion in a single step 810. These different steps are indeed performed conjointly/simultaneously in a single and same vial at 50° C., under ultrasound for 30 minutes. Thus, there is no need to perform manual interventions between these steps, nor to add reagents during the method. The protocol P2 is therefore easy to automate, avoids possible errors of manipulation and permits the use of smaller volumes. Moreover, it also allows the analysis of complex samples (urine, plasma, cerebrospinal fluid), such as explained above.

This protocol P2 gives similar results (LC-ESI-MS analyses) to the results of the protocol P1 described in example 2, for two of the three microorganisms assayed: *Escherichia coli* (Gram-) and *Staphylococcus epidermidis* (Gram+) both in number of peptides and in cumulated area.

Equipment and Method 3.1 Products Used

Formic acid/Fluka/reference: 06450
Iodoacetamide, (IAA)/Sigma/16125-5G/MM=184.96
Tris(2-carboxyethyl)phosphine (TCEP) hydrochloride 0.5 M solution/Sigma/646547
Ammonium bicarbonate/Sigma/A6141-500 g/MM=79.06
Ammonium hydroxide, NH$_4$OH/28% ammonia/reference: 21190292/MM=17.03 g
Trypsin/Promega/reference V511 (storage at −20° C.)
"Suspension medium" (sterile water) bioMérieux (ref.: 70640)
*Escherichia coli* strain ATCC No.: 11775T
*Staphylococcus epidermidis* strain ATCC No.: 14990
*Candida albicans* strain, ATCC No.: 18804

3.2 Preparation of the Buffer Solutions

Buffer No. 4: 50 mM ammonium bicarbonate pH8/storage 1 month at +4° C.
For 50 ml buffer: 197.6 mg of bicarbonate qsp 50 ml H$_2$O/pH=7.9; approximately 10 µl addition of NH$_4$OH to obtain pH=8
Buffer No. 5': 150 mM TCEP/to be prepared extemporaneously/dilution in buffer no. 4
Buffer No. 6: 150 mM IAA/to be prepared extemporaneously
For 1 ml buffer: 27.7 mg of IAA qsp 1 ml bicarbonate buffer No. 4

3.3 Equipment

Centrifuge "APPLI 24"/Prolabo
1.5 ml vials; "Safe Lock" Eppendorf,ef 0030120.086
Centrifuge "benchtop"/Eppendorf/ref 5415C
Spectrophotometer UVIKON+80 µl quartz cuvettes
BMX culture dishes BMX: COS (ref.: 43041) and SDA (ref.: 43555)
Ultrasound probe "Hielscher"; ref: PN-66-NNN
0.1 mm lysis beads (small diameter): "Zirconia/Silica beads"/Roth/N033.1
1 mm lysis beads (large diameter): "Silibeads typ 1/1.3 mm; ref: 4504/VWR
Bridges/Dutscher/reference: 011870A 3.4 Protocol 3.4.1. Preliminary Steps 800, 802, 804 and 806

In practice, firstly buffer solutions No. 5' (dilution of a solution of 500 mM TCEP to 150 mM in bicarbonate buffer No. 4) and No. 6 (27.7 mg/ml of IAA in bicarbonate buffer No. 4) are prepared.

Then, using a "spoon" spatula, 50 mg of beads of 0.1 mm diameter and 50 mg of beads of 1 mm diameter are weighed and are introduced into a vial with a capacity of 1.5 ml. As indicated above, the mixture of the beads of "small diameter" and of "large diameter" is designated by the numerical reference 8061, still in FIG. 8.

One to three colonies 110 are taken from a Petri dish 100, which are placed in suspension in water in step 800. The concentration of bacteria in the suspension thus obtained is estimated by conventional turbidity measurement methods (measurement of absorption at 550 nm). A volume of suspension corresponding to 1.108 CFU is taken and then centrifuged in step 802, at 4000 rpm for 5 minutes at ambient temperature. At the end of this centrifugation step 802, the pellet is adsorbed (ECS, CA16 and SE9) in step 804 in 100 µl of No. 4 buffer solution vial No. 2) and then, still in step 804, are added 3.5 µl of 150 mM TCEP (buffer No. 5') to obtain a final TCEP concentration of 5 mM in vial No. 2. Vortexing is applied for 2 seconds (maximum power) to homogenise the contents of this vial No. 2 and this mixture is pipetted in order to transfer it, in step 806, into vial No. 1 containing the 8061 beads. Vial No. 2 is then eliminated.

3.4.2. Steps 808, 810 and 812

Then are introduced into vial No. 1, in step 808:

9 µl of solution of 150 mM IAA (buffer No. 6) in order to obtain a final molarity of 12.5 mM; and 10 µl of 1 µg/µl trypsin.

Following this, vortexing is applied for 2 seconds (maximum power) for homogenisation.

A bridge is placed on vial No. 1 to prevent it from opening during lysis by sonication.

This vial No. 1 is then introduced into one of the orifices of the Hielscher probe (the 6 orifices at the end of the probe are supposed to be identical according to the supplier), and then 30 minutes are timed (settings Amplitude 100/Cycle 0.5) in order to allow the reactions of lysis, of reduction, of alkylation and of tryptic digestion to take place conjointly/simultaneously. The temperature of the mixture in vial No. 1, at step 810, reaches approximately 50° C.

Vial No. 1 is then removed from the orifice of the probe by means of a "lever" holding the vial by the bridge, and then this vial No. 1 is cooled, in step 812, by storing it for 1 minute in ice in order to return the temperature of the mixture in the vial to ambient temperature.

Summarising, the main step 810 allows the conjoint/simultaneous occurrence of:

a. Lysis of the bacteria/reduction of the proteins (TCEP breaks the disulphide bridges): obtaining of the denatured/reduced proteins b. Alkylation: step of locking the disulphide bridges of the proteins by methylation with IAA c. Tryptic digestion of the proteins: obtaining the peptides.

3.4.3. Stopping the Tryptic Digestion 814

Stopping the tryptic digestion is performed by addition of formic acid (qsp pH below 4) in vial No. 1, in step 814. As indicated above, the fact of lowering the pH below 4 reversibly inactivates the enzymatic activity of trypsin.

The pH of the sample is approximately 8 (pH verified with the pH meter/microtube special probe) before the addition of 0.5 µl of formic acid. It is approximately 3 after addition of the latter in step 814. The mixture is then vortexed for 2 seconds (maximum power) for homogenisation.

3.4.4. Steps 816, 818, 820 and 822

The peptides obtained at the end of the main step 810 are in the supernatant. The latter is therefore pipetted (a part of the 0.1 mm beads is often recovered) and transferred, in step 816, into another vial (vial No. 3), and then centrifuged, in step 818, for 30 minutes, at 15000 g and at 4° C.

90 µl of supernatant comprising the peptides are then recovered in step 820 and introduced into another vial (vial No. 4) in step 822. The latter is stored in the freezer at a temperature of −20° C.

3.5. Validation of the Results

The peptides contained in vial No. 4 are then analysed by LC-ESI-MS in order to determine the quality/efficiency of lysis protocol P2 (step of validation of the results). The results, for each of the three microorganisms studied, are presented in FIG. 9. Said protocol P2 is designated "P2-TCEP" in this FIG. 9, with reference to the TCEP, used as a denaturing agent in the present example 3.

As explained above, the values shown in this FIG. 9 correspond to the numbers of the correctly detected targeted peptides as well as to the cumulated area under the peak of these peptides in the mass spectrum obtained by LC-ESI-MS in MRM mode.

Figure 9:
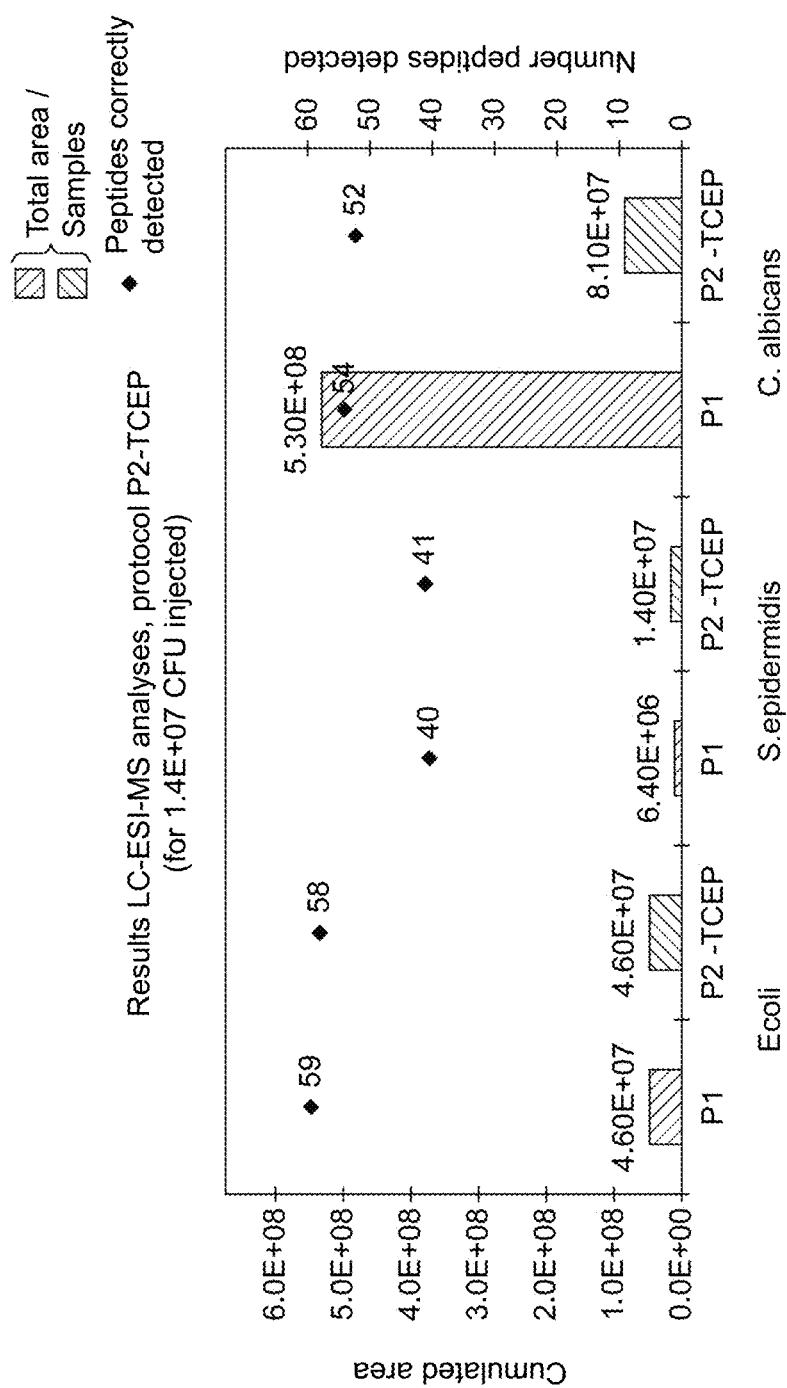
FIG. 9 is a graph showing the results of the LC-ESI-MS analyses performed at the end of the P2-TCEP protocol on each of the above-mentioned three microorganisms, i.e. *Escherichia coli* ECS, *Staphylococcus epidermidis* SE9 and *Candida albicans* CA16.

As shown in this FIG. 9, this protocol P2 produces similar results to those obtained by the above-mentioned protocol P1 for two of the three microorganisms assayed, i.e. *Escherichia coli* and *Staphylococcus epidermidis*. The results obtained for *Candida albicans* are satisfactory for the number of peptides.

As indicated above, the methods (protocols) of obtaining peptides according to the present invention fall within the framework of the preparation of samples of procaryotic and/or eucaryotic cells for their subsequent analysis.

Example 4: Protocol P2 with DTT ("P2-DTT")

The protocol P2 the object of example 3 above was reproduced replacing the TCEP with another denaturing agent, i.e. DTT. For purposes of clarity, this method P2 with DTT is called "P2-DTT".

Figure 10:
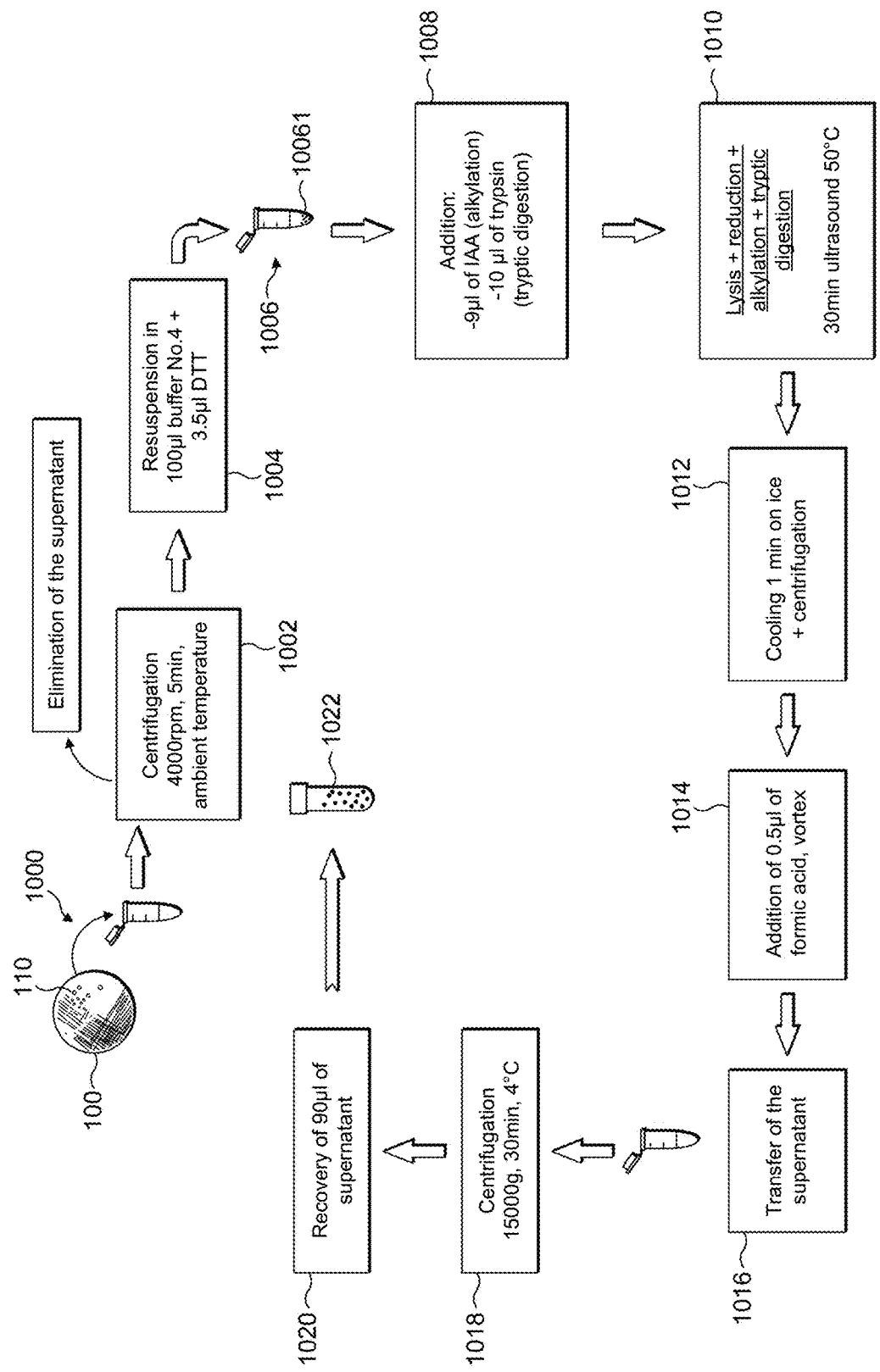
FIG. 10 is a diagram showing the different steps of the method according to the third, particularly advantageous aspect of the present invention (P2), in which the denaturing agent used is DTT (P2-DTT)

The protocol P2-DTT is described below, with reference to FIG. 10.

The protocol P2-DTT gives similar results (LC-ESI-MS analyses) to the protocol P1 described in example 2, for two of the three microorganisms assayed: *Escherichia coli* (Gram-) and *Staphylococcus epidermidis* (Gram+) both in number of peptides and in cumulated area.

Equipment and Method 4.1 Products Used

Formic acid/Fluka/reference: 06450

Iodoacetamide, (IAA)/Sigma/16125-5G/MM=184.96

DL-1,4-Dithiothreitol 99%, (DTT)/Acros/165680010/lotA0269816/MM=154.24

Ammonium bicarbonate/Sigma/A6141-500 g/MM=79.06

Ammonium hydroxide, $NH_4OH/28\%$ ammonia/reference: 21190292/MM=17.03 g

Trypsin/Sigma/T0303 (storage at −20° C.)

"Suspension medium" (sterile water) bioMérieux (ref.: 70640)

*Escherichia coli* strain, ATCC No.: 11775T

*Staphylococcus epidermidis* strain, ATCC No.: 14990

*Candida albicans* strain, ATCC No.: 18804

4.2 Preparation of the Buffer Solutions

Buffer No. 4; 50 mM ammonium bicarbonate pH8/storage 1 month at +4° C. For 50 ml buffer: 197.6 mg of bicarbonate qsp 50 ml H2O/pH=7.9; addition of approximately 10 µl of $NH_4OH$ to obtain pH=8

Buffer No. 5: 150 mM DTT/to be prepared extemporaneously

For 1 ml of buffer: 23.1 mg of DTT qsp 1 ml bicarbonate buffer No. 4

Buffer No. 6: 150 mM IAA 150 mM/to be prepared extemporaneously

For 1 ml buffer: 27.7 mg of IAA qsp 1 ml bicarbonate buffer No. 4

4.3 Equipment

Centrifuge "APPLI 24"/Prolabo 1.5 ml vials; "Safe Lock" Eppendorf, ref: 0030120.086

Centrifuge "benchtop"/Eppendorf/ref 5415C

Spectrophotometer UVIKON+80 µl quartz cuvettes

BMX culture dishes: COS (ref.: 43041) and SDA (ref.: 43555)

Ultrasound probe "Hielscher"; ref. PN-66-NNN 0.1 mm lysis beads (small diameter): "Zirconia/Silica beads"/Roth/N033.1

1 mm lysis beads (large diameter): "Silibeads typ 1/1.3 mm/ref: 4504/VWR

Bridges/Dutscher/reference: 011870A 4.4 Protocol 4.4.1. Preliminary Steps 1000, 1002, 1004 and 1006

Firstly, the buffer solutions No. 5 (150 mM DTT) and No. 6 (150 mM IAA) are prepared.

Then, using a "spoon" spatula, 50 mg of 0.1 mm diameter beads and 50 mg of 1 mm diameter beads are weighed and are introduced into a vial with a capacity of 1.5 ml. As indicated above, the mixture of the beads of "small diameter" and of "large diameter" is designated by the numerical reference 10061, still in FIG. 10.

One to three colonies are taken 110 from a petri dish 100, and are placed in suspension in water in step 1000. The concentration of bacteria in the suspension thus obtained is estimated by conventional methods of turbidity measurement (measurement of absorption at 550 nm). A volume of suspension corresponding to $1.10^8$ CFU is taken and then centrifuged in step 1002, at 4000 rpm for 5 minutes at ambient temperature. At the end of this step of centrifugation 1002, the pellet is adsorbed (ECS, CA16 and SE9) in step 1004 in 100 μl of the buffer solution No. 4 (Vial No. 2), then, still in step 1004, are added 3.5 μl of 150 mM DTT (buffer No. 5) to obtain a final DTT concentration of 5 mM in vial No. 2. Vortexing is applied for 2 seconds (maximum power) to homogenise the contents of this vial No. 2 and this mixture is pipetted in order to transfer it, in step 1006, into vial No. 1 containing the 10061 beads. Vial No. 2 is then eliminated.

4.4.2. Steps 1008, 1010 and 1012

Into vial No. 1, in step 1008, are then introduced:
9 μl of 150 mM solution of IAA (buffer No. 6) in order to obtain a final molarity of 12.5 mM; and
10 μl of 1 μg/μl trypsin.

After that, vortexing is applied for 2 seconds (maximum power) for homogenisation. A bridge is placed on vial No. 1 to prevent it from opening during lysis by sonication.

This vial No. 1 is then introduced into one of the orifices of the Hielscher probe (the 6 orifices at the end of the probe are supposed to be identical according to the supplier), and then 30 minutes are timed (settings Amplitude 100/Cycle 0.5) in order to allow the reactions of lysis, of reduction, of alkylation and of tryptic digestion to take place conjointly/simultaneously. The temperature of the mixture in vial No. 1, at step 1010, reaches approximately 50° C.

Vial No. 1 is then removed from the orifice of the probe by means of a "lever" holding the vial by the bridge, and then this vial No. 1 is cooled, in step 1012, by storing it for 1 minute in ice in order to return the temperature of the mixture of the vial to ambient temperature.

Summarising, the main step 1010 allows taking place conjointly/simultaneously of:
a. Lysis of the bacteria/reduction of the proteins (DTT breaks the disulphide bridges): obtaining of the denatured/reduced proteins
b. Alkylation: step of locking the disulphide bridges of the proteins by methylation with IAA
c. Tryptic digestion of the proteins: obtaining of the peptides.

4.4.3. Stopping the Tryptic Digestion 1014

Stopping the tryptic digestion is performed by addition of formic acid (qsp pH lower than 4) in vial No. 1, in step 1014. As indicated above, the fact of lowering the pH below 4 reversibly disables the enzymatic activity of trypsin.

The pH of the sample is approximately 8 (pH verified with the pH meter/microtube special probe) before the addition of 0.5 μl of formic acid. It is approximately 3 after addition of the latter in step 1014. The mixture is then vortexed for 2 seconds (maximum power) for homogenisation.

4.4.4. Steps 1016, 1018, 1020 and 1022

The peptides obtained at the end of the main step 1010 are in the supernatant. The latter is therefore pipetted (a part of the 0.1 mm beads is often recovered) and transferred, in step 1016, into another vial (vial No. 3), and then centrifuged, in step 1018, for 30 minutes, at 15000 g and at 4° C.

90 μl of supernatant comprising the peptides are then recovered in step 1020 and introduced into another vial (vial No. 4) in step 1022. The latter is stored in the freezer at a temperature of −20° C.

4.5. Validation of the Results

The peptides contained in vial No. 4 are then analysed by LC-ESI-MS in order to determine the quality/efficiency of the lysis protocol P2-DTT (step of validation of the results). The results, for each of the three microorganisms studied, are presented in FIG. 11.

As explained above, the values shown in this FIG. 11 correspond to the numbers of targeted peptides correctly detected as well as to the cumulated area under the peak of these peptides in the mass spectrum obtained by LC-ESI-MS in MRM mode.

Figure 11:
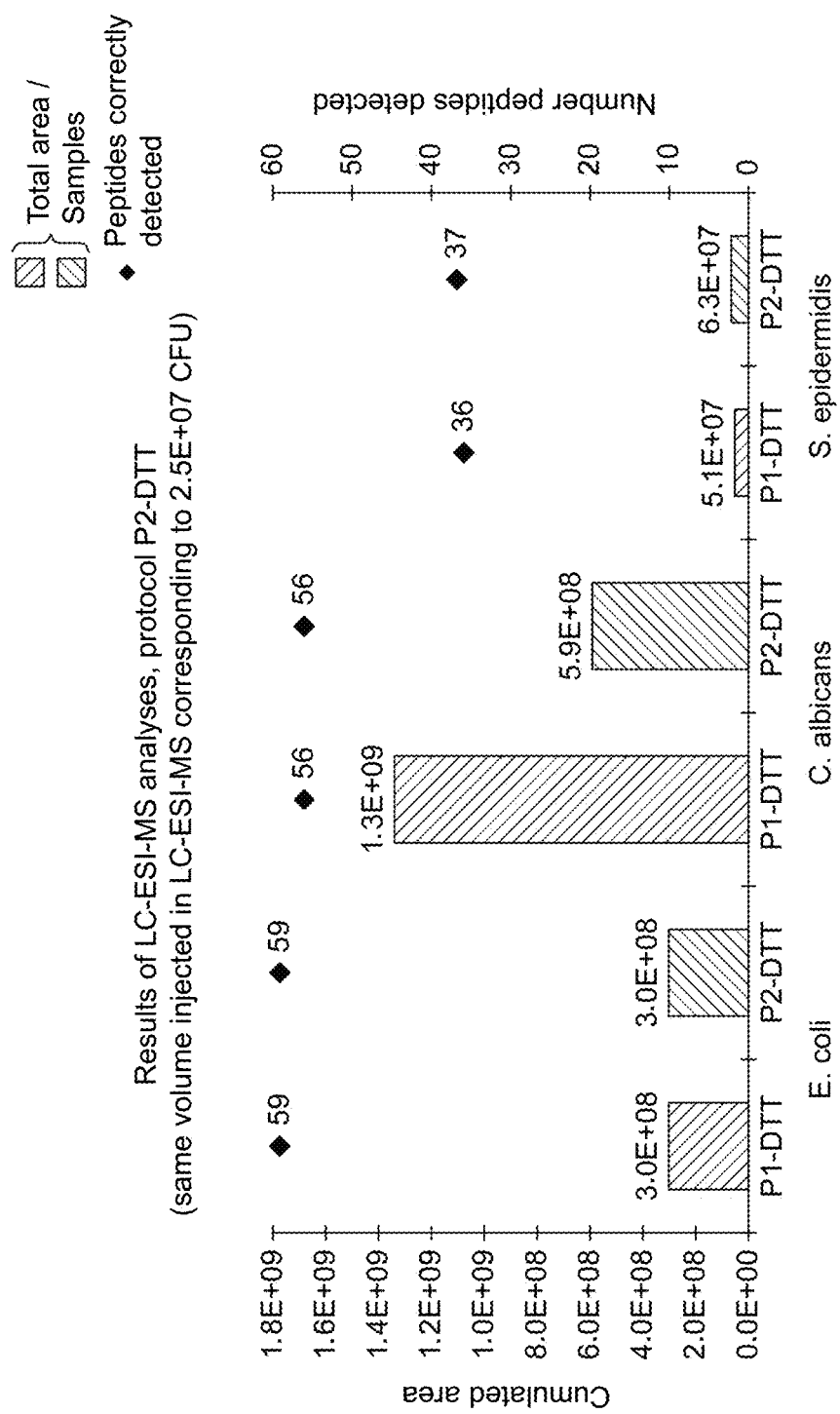
FIG. 11 is a graph showing the results of the LC-ESI-MS analyses performed at the end of the P2-DTT protocol on each of the above-mentioned three microorganisms, i.e. *Escherichia coli* ECS, *Staphylococcus epidermidis* SE9 and *Candida albicans* CA16.

As shown in this FIG. 11, this protocol P2 with DTT produces results similar to those obtained by the protocol P1 mentioned above for two of the three microorganisms assayed, i.e. *Escherichia coli* and *Staphylococcus epidermidis*. The results obtained for *Candida albicans* are satisfactory for the number of peptides.

Moreover, it proves that the use of DTT instead of TCEP as denaturing agent has no apparent impact either on the number of peptides or on the overall cumulated area.

As indicated above, the methods (protocols) of obtaining peptides according to the present invention fall within the framework of the preparation of samples of procaryotic and/or eucaryotic cells for their subsequent analysis.

The analysis of these samples can in particular allow biomarker research and can be applied, inter alia, to the analysis of complex biological samples such as plasma, urine, cerebrospinal fluid, etc.

In the field of microbiology, the peptides obtained by the method according to the invention can allow the characterisation of at least one microorganism from a sample, comprising for example, the identification of said microorganism and the determination of the properties of typing, potential resistance to at least one antimicrobial and virulence factor relating to said microorganism.

This method of characterisation of at least one microorganism can prove particularly useful in the medical, pharmaceutical or agro-food field.

The determination of the properties of typing, resistance to at least one antimicrobial and virulence factor is performed by mass spectrometry using proteins, peptides and/or metabolics as markers of said properties of typing, resistance to at least one antimicrobial and virulence factor. Preferably the mass spectrometry is of MS/MS type, advantageously this mass spectrometry is MRM.

Preferably, the determination of the products of typing, resistance to at least one antimicrobial and virulence factor is performed in the same mass spectrometry apparatus simultaneously.

Optimally, mass spectrometry of MS/MS type, and advantageously of MRM type, can be envisaged as the step of confirmation of to confirm the identification of the microorganism.

Indeed, the characterisation of the microorganisms is fundamental both in the clinical field and in the industrial field. Thus, for example, the identification of resistance to antimicrobials such as antibiotics, and the detection of virulence factors are essential elements for ensuring optimal treatment of patients. Similarly, typing is crucial for epidemiological studies and for combating nosocomial illnesses.

By typing of a microorganism, is understood the differentiation of several strains within a same species. Typing has an epidemiological value, the clinician knows whether the strain isolated in the patient comes from the same source as other apparently identical strains isolated in other patients or in the environment. This thus allows the source of infection to be revealed within a hospital or in the case of food poisoning. As non-limiting examples of markers of properties of typing in bacteria, can be cited peptides presenting characteristic mutations such as the transcription products of the genes adk, fumC, gyrB, icd, mdh, purA and recA of *Escherichia coli*, and those of the genes arc, aroE, glpF, gmk, pta, tpi and yqiL of *Staphylococcus aureus*. As non-limiting examples of markers of typing properties in the protozoa, can be cited the products of the chitinase gene of *Entamoeba histolytica* and *E. dispar*. As non-limiting examples of markers of typing properties in the viruses, can be cited the products of the polymerase gene of the human immunodeficiency virus. Lastly, as non-limiting examples of markers of typing properties in yeasts, can be cited the transcription products of the gene fragments aat1a, acc1, adp1, mpib, sya1, vps13, and zwf1b of *Candida albicans*.

By determination of the resistance to at least one antimicrobial, is understood the determination of the susceptibility of a microorganism to be destroyed by an antimicrobial. Thus, if the microorganism is a bacterium, the antimicrobial against which it can develop a resistance is an antibiotic, if it is a protozoan, the antimicrobial is an antiparasitic, if it is a virus, the antimicrobial is an anti-viral, and, if it is a yeast, the antimicrobial is an antifungal The proteins involved in the resistance mechanisms will differ depending on the family and the species. As non-limiting examples of markers of resistance to at least one antibiotic useful with bacteria, can be cited the transcription products of the MecA gene of *Staphylococcus aureus*, conferring resistance to Methicillin, and permitting indication of whether the strains are methicillin-resistant (MRSA strains) or methicillin-sensitive (MSSA strains). The protein TEM-2 can also be cited which permits indication of whether the strains of *Escherichia coli* are resistant to the penicillins but sensitive to other classes of antibiotics of the cephalosporin or carbapenem type. Another marker is the enzyme called KPC (for *Klebsiella Pneumoniae* Carbapenemase) which confers resistance to the carbapenems. Another example of a resistance marker for *Staphylococcus aureus* is the metabolic profile representative of resistance to vancomycin such as described by Alexander E. et al in the poster "Metabolomics-based approach to antibiotic resistance in *Staphylococcus aureus*" presented to the ASMS congress, 2009. As a non-limiting example of markers of resistance to at least one antiparasitic useful with protozoans, can be cited dismutase superoxide containing iron (Fe-SOD) and peroxiredoxin increased expression of which confers resistance to metronidazole. As a non-limiting example of marker of resistance to at least one anti-viral useful with the viruses, can be cited the mutations of the reverse transcriptase enzyme of the human immunodeficiency virus, conferring reduced sensitivity to the nucleoside reverse transcriptase inhibitors. Lastly, as a non-limiting example of markers of resistance to at least one antifungal useful with the yeasts, can be cited the mutation of the enzyme 1-3-b-D-glucane synthase of *Candida albicans*, conferring a reduced sensitivity to the echinocandins. As a further example, can be mentioned resistance to the azole antifungals in *Candida albicans*, in particular resistance to fluconazole. The target of fluconazole is an enzyme, lanosterol demethylase, involved in the synthesis of ergosterol, the main constituent of the fungal wall. Resistance to fluconazole can be associated with the appearance of point mutations in the erg11 gene coding for lanosterol demethylase.

By determination of the virulence of a microorganism, is understood the evaluation of the pathogenic, harmful and virulent nature of the microorganism. As non-limiting examples of virulence markers in the bacteria, can be cited PVL (Panton-Valentine Leukocidin), a cytolytic toxin with two synergistic components (Lukfet LukS), present in *Staphylococcus aureus*, which is one of the most virulent toxins causing skin involvements, extensive cellulitis, osteomyelitis and necrotising pneumonias, and is involved in viral superinfections. Other examples comprise Autolysin and Pneumolysin present in *Streptococcus pneumoniae*, a species responsible for infections of the respiratory tracts, for meningitis and for bacteremia, as well as the A and B toxins of *Clostridium difficile*, a commensal bacterium of the intestine, which either cause damage to the permeability of the intestinal epithelium (A toxin) or directly attack the cells of the epithelium (B toxin), or in time reduce the intestinal transit and the intestinal absorption, causing diarrhoea (combined action of the A and B toxins). The Shiga toxins Stx1 and Stx2 present in *Escherichia coli* can also be cited as an example. These two cytotoxins are considered as important virulence factors of the enterohaemorrhagic *Escherichia coli*. They are responsible for complications such as haemorrhagic colitis or uremic haemolytic syndrome. As a non-limiting virulence marker in the protozoans, can be cited antioxidants (Fe-hydrogenase 2, peroxiredoxin, dismutase superoxide) present in *Entamoeba histolytica*, a species responsible for dysentery, hepatic abscess. As a non-limiting example of virulence markers in the viruses, can be cited the variant of the Nef protein in the type-1 human immunodeficiency virus, the most pathogenic type in the human being. Lastly, as a non-limiting virulence marker in the yeasts, can be cited lipase 8 in *Candida albicans*, a species responsible for superficial candidiasis but also septicaemic and disseminated candidiasis. It should be noted that the specific virulence markers are also usable as typing marker.

By way of example of bacteria being able to be characterised by an analysis method of this type, can be cited:
  *Escherichia coli* using TEM-2 as a resistance and typing marker, as well as Shiga toxins, OmpA as a virulence and typing marker.
  *Enterococcus faecalis* and *faecium* using VanA and VanB for resistance and typing, as well as ESP (Enterococcal Surface Protein) for virulence and typing, or
  *Staphylococcus aureus* using the protein called immunoglobulin G-binding protein A (also called protein A) for typing, the protein PBP2a for resistance, or even typing, as well as the protein PVL for virulence, or even also typing.

As other microorganisms able to be characterised by the above-mentioned analysis method, can be cited:
  *Candida albicans* using the enzyme 1-3-b-D-glucane synthase or the enzyme lanosterol demethylase as a resistance and typing marker, as well as lipase 8 as a virulence and typing marker.

The procaryotic and/or eucaryotic cells according to the present invention can be obtained from any sample able to contain a target microorganism. The sample can be of biological origin, either animal, vegetable or human. It can then correspond to a biological fluid sample (whole blood, serum, plasma, urine, cerebrospinal fluid, organic secretion, for example), a tissue sample or isolated cells. This sample can be used as such to the extent that the characterisation markers of the microorganisms are available in the assayed sample, or it can be subjected, prior to analysis, to preparation of enrichment, extraction, concentration, purification, culture type, according to methods known to the man skilled in the art.

The sample can be of industrial origin, or, according to a non-exhaustive list an air sample, water sample, sample taken from a surface, a piece or a manufactured product, a product of food origin. Of the samples of food origin, can be cited non-exhaustively a milk product sample (yoghurts, cheeses), meat, fish, egg, fruit, vegetable, water, beverage (milk, fruit juice, soda, etc.). These samples of food origin can also come from sauces or prepared dishes. A food sample can lastly come from an animal feed, such as in particular animal meals.

The mass spectrometry to be employed in the method of analysis according to the invention is widely known to the man skilled in the art as a powerful tool for the analysis and the detection of different types of molecules. Generally, any type of molecule able to be ionised can be detected as a function of its molecular mass by means of a mass spectrometer. Depending on the nature of the molecule to be detected, of protein or metabolic origin, certain mass spectrometry technologies can be more suited. Nevertheless, whatever the mass spectrometry method used for the detection, the latter comprises a step of ionisation of the target molecule into ions known as molecular, in the present case a step of ionisation of the characterisation markers, and a step of separation of the molecular ions obtained as a function of their mass.

All mass spectrometers therefore include:
i) an ionisation source intended to ionise the markers present in the sample to be analysed, i.e. to confer a positive or negative charge to these markers;
ii) a mass analyser intended to separate the ionised markers, or molecular ions 15, as a function of their mass over charge (m/z) ratio;
iii) a detector intended to measure the signal produced either directly by the molecular ions, or by ions produced from the molecular ions, as detailed below.

The ionisation step necessary for the use of a mass spectrometer can be performed by any method known to the man skilled in the art. The ionisation source allows the molecules to be assayed to be brought into a gaseous and ionised state. An ionisation source can be used either in positive mode to study positive ions, or in negative mode to study negative ions. Several types of sources exist and will be used depending on the required result and the molecules analysed. In particular can be cited:
  electronic ionisation (EI), chemical ionisation (CI) and desorption chemical ionisation (DCI)
  bombardment by fast atoms (FAB), metastable atoms (MAB) or ions (SIMS, LSIMS)
  inductive plasma coupling (ICP)
  chemical ionisation at atmospheric pressure (APCI) and photoionisation at atmospheric pressure (APPI)
  electronebulisation or electrospray (ESI)
  laser-assisted desorption-ionisation by MALDI matrix, surface-activated or on silicon
  ionisation-desorption by interaction with metastable species (DART).

In particular, the ionisation can be employed as follows: the sample containing the target molecules is introduced into an ionisation source, in which the molecules are ionised in the gaseous state and thus transformed into molecular ions which correspond to the initial molecules. An ionisation source of electrospray type (ESI for ElectroSpray Ionisation) permits ionisation of a molecule while causing it to pass from a liquid state to a gaseous state. The molecular ions obtained then correspond to the molecules present in the liquid state, with in positive mode one, two, or even three additional protons or more, and are therefore carriers of one, two, or even three charges or more. For example when the target molecule is a protein, ionisation of the proteotypic peptides obtained after fractionation of the target protein, by means of a source of electrospray type operating in positive mode, leads to polypeptide ions in the gaseous state, with one, two, or even three additional protons or more which are therefore carriers of one, two, or even three charges or more, and permits passage from a liquid state to a gaseous state This type of source is particularly well suited, when the target molecules or proteotypic peptides obtained are previously separated by reverse-phase liquid chromatography. Nevertheless, the ionisation yield of the molecules present in the sample can vary depending on the concentration and the nature of the different species present. This phenomenon results in a matrix effect well known to the man skilled in the art.

A MALDI ionisation source will permit ionisation of the molecules, from a sample in the solid state.

The mass analyser in which the separation of the ionised markers as a function of their mass/charge (m/z) ratio is performed is any mass analyser known to the man skilled in the art. Low resolution analysers, of quadripole or quadrupole (Q), 3D (IT) or linear (LIT) ion trap, also called ionic trap, type and high resolution analysers, permitting measurement of the exact mass of the analytes and which use in particular the magnetic sector coupled with an electric sector, the time of flight (TOF) can be cited.

The separation of the molecular ions as a function of their m/z ratio can be employed once (simple mass spectrometry or MS), or several successive MS separations can be performed. When two successive MS analyses are performed, the analysis is called MS/MS or MS2. When three successive MS separations are performed the analysis is called MS/MS/MS or MS3 and more generally, when n successive MS separations are performed, the analysis is called MSn.

Of the techniques employing several successive separations, modes SRM (Selected Reaction Monitoring) in case of detection or assay of a single target molecule, or MRM (Multiple Reaction Monitoring) in case of detection or assay of several target molecules, are particular uses of MS2 separation. Similarly MRM3 mode is a particular use of MS/MS/MS separation. It is then called targeted mass spectrometry.

In the case of detection in simple MS mode, it is the mass/charge ratio of the molecular ions obtained which is correlated with the target molecule to be detected.

In the case of detection in MS/MS mode, essentially two steps are added, relative to an MS assay which are:
i) fragmentation of the molecular ions, then called precursor ions, to give ions called 1st generation fragment ions, and
ii) separation of the ions called 1st generation fragment ions as a function of their mass (m/z) 2, the ratio (m/z)1 corresponding to the (m/z) ratio of the precursor ions.

It is then the mass/charge ratio of the 1st generation fragment ions thus obtained which is correlated with the target molecule to be detected. By first generation fragment ion, is understood an ion emanating from the precursor ion following a fragmentation step and the mass over charge m/z ratio of which is different from the precursor ion.

The pairs (m/z)1 and (m/z)2 are termed transitions and are representative of the characteristic ions to be detected.

The choice of the characteristic ions which are detected to be correlated with the target molecule is made by the man skilled in the art according to standard methods. Their selection will advantageously lead to the most sensitive, the most specific and the most robust assays possible, in terms of reproducibility and reliability. In the methods developed for the selection of proteotypic $(m/z)_1$, and of first generation fragment $(m/z)_2$ peptides, the choice is essentially based on the intensity of the response. For more details, reference can be made to V. Fusaro et al. Commercial software, such as the MIDAS and MRM Pilot software by Applied Biosystems or MRMaid can be used by the man skilled in the art to allow him to predict all the possible transition pairs. He can also have recourse to a database called PeptideAtlas, constructed by F. Desiere et al. to compile all of the MRM transitions of peptides described by the scientific community. This PeptideAtlas base is available on a free access basis on the internet.

An alternative approach to select the proteotypic peptides (obtained for example by tryptic digestion; cf. above) $(m/z)_1$ and $(m/z)_2$, consists in using the MS/MS fragmentation spectra obtained during other works. These works can be, for example, the phases of discovery and of identification of the biomarkers by proteomic analysis. This approach has been proposed by Thermo Scientific at a users meeting It permits generation of a list of candidate transitions from peptides experimentally identified by the SIEVE software (Thermo Scientific). Certain criteria have been detailed by J. Mead et al. for the choice of $(m/z)_1$ and $(m/z)\ 2$ and are detailed below:

- Peptides with internal cleavage sites, i.e. with internal Lysine or Arginine, must be avoided, unless the Lysine or Arginine is followed by Proline,
- Peptides with Asparagine or Glutamine must be avoided as they can deaminate,
- Peptides with Glutamine or Glutamic Acid at the N-terminal must be avoided as they can spontaneously form into a ring,
- Peptides with Methionine must be avoided as they can be oxidised,
- Peptides with Cysteine must be avoided as they can be modified in a non-reproducible manner at a possible step of denaturation, reduction and locking of the thiol functions,
- Peptides with Proline can be considered as favourable because they generally produce intense fragments under MS/MS with a single very major peak. However, a single very major fragment does not permit validation of the identity of the transition in a complex mixture. Indeed, only the simultaneous presence of several characteristic fragments permits verification that the precursor ion sought has indeed been detected,
- Peptides having a Proline adjacent to the C-terminal (position n-1) or in the second position relative to the C-terminal (position n-2) are to be avoided as, in this case, the size of the first generation peptide fragment is generally considered as too small to be sufficiently specific,
- The selection of fragments having a mass greater than the precursor is to be preferred to promote specificity. For this purpose, it is necessary to select a discharge precursor ion and select the most intense first generation fragment ion having a mass greater than the precursor, i.e. a first generation fragment ion with a single charge.

The fragmentation of the selected precursor ions is performed in a fragmentation cell such as models of triple quadripole type or of ion trap type or of time of flight (TOF) type which also permit the separation of the ions. The fragmentation or fragmentations will be performed conventionally by collision with an inert gas such as argon or nitrogen, in an electric field, by photo-excitation or photodissociation using an intense light source, collision with electrons or radical species, by application of a potential difference, for example in a time of flight tube, or by any other method of activation. The characteristics of the electric field determine the intensity and the nature of the fragmentation. Thus, the electric field applied in the presence of an inert gas, for example in a quadripole, determines the collision energy contributed to the ions. This collision energy will be optimised, by the man skilled in the art, to increase the sensitivity of the transition to be assayed. As an example, it is possible to vary the collision energy between 5 and 180 $e^-V$ under q2 in an AB SCIEX QTRAP® 5500 mass spectrometer by the company Applied Biosystems (Foster City, United States of America). Similarly, the duration of the collision step and the excitation energy in, for example, an ion trap will be optimised, by the man skilled in the art to lead to the most sensitive assay. As an example, it is possible to vary this duration, termed excitation time, between 0.010 and 50 ms and the excitation energy between 0 and 1 (arbitrary unit) under Q3 in an AB SCIEX QTRAP®5500 mass spectrometer by the company Applied Biosystems.

Lastly, the detection of the selected characteristic ions is effected in conventional manner, in particular by means of a detector and of a processing system. The detector collects the ions and produces an electrical signal the intensity of which depends on the quantity of irons collected. The signal obtained is then amplified for it to be able to be processed by computer technology. A computer technology unit for processing the data allows the data received by the detector to be converted into a mass spectrum.

The principle of the SRM mode, or of the MRM mode, is to specifically select a precursor ion, to fragment it, and then to specifically select one of its fragment ions. For such applications, devices of the triple quadripole or triple quadripole with ion trap hybrid type are generally used.

In the case of a triple quadripole device (Q1q2Q3) used in $MS^2$ mode, for the assay or the detection of a target protein, the first quadripole (Q1) permits filtration of the molecular ions, corresponding to the proteotypic peptides characteristic of the protein to be assayed and obtained at a prior digestion step, as a function of their mass over charge (m/z) ratio. Only the peptides having the mass/charge ratio of the proteotypic peptide sought, ratio called $(m/z)_1$, are transmitted into the second quadripole (q2) and act as precursor ions for the subsequent fragmentation. The q2 analyser permits fragmentation of the peptides of mass/charge ratio $(m/z)_1$ into first-generation fragment ions. The fragmentation is generally obtained by collision of the precursor peptides with an inert gas, such as nitrogen or argon in q2. The first-generation fragment ions are transmitted into a third quadripole (Q3) which filters the first-generation fragment ions as a function of a specific mass over charge ratio, which ratio is called $(m/z)_2$.

Only the first-generation fragment ions having the mass/charge ratio of a fragment characteristic of the proteotypic peptide sought $(m/z)_2$ are transmitted into the detector to be detected, or even quantified.

This mode of operation presents double selectivity, relative to the selection of the precursor ion on the one hand and selection of the first-generation fragment ion on the other. Mass spectrometry in SRM or MRM mode is therefore advantageous for quantification.

When the mass spectrometry employed in the method of the invention is tandem mass spectrometry (MS2, MS3, MS4 or MS5), several mass analysers can be linked together. For example, a first analyser separates the ions, a collision cell allows fragmentation of the ions, and a second analyser separates the fragment ions. Certain analysers, such as ion traps or FT-ICR, constitute several analysers in one and permit fragmentation of the ions and analyse the fragments directly.

According to preferred embodiments of the invention, the method of the invention comprises one or more of the following characteristics:
  the mass spectrometry, employed for the properties of typing, of potential resistance to at least one antimicrobial and virulence factor, is spectrometry of MS/MS type, which has the advantage of generating a specific fragment of the molecule to be detected or to be quantified, and thus brings great specificity to the assay method;
  the MS/MS spectrometry is MRM, which has the advantage of using an analysis cycle time in the mass spectrometer of some tens of milliseconds, which permits detection or quantification with high sensitivity, and in multiplexed manner, of a large number of different molecules;
  the determination of the properties of typing, resistance to an antimicrobial and virulence factor is performed in the same mass spectrometry apparatus, preferably simultaneously, which has the advantage of reducing the analysis time and the cost of the instrument, this also facilitates the processing and the presentation of the results.

In addition to the determination of the properties of typing, resistance to an antimicrobial and virulence factor, it is advisable to identify the microorganism or microorganisms present in the sample to be assayed.

The methods of identification of microorganisms are widely known to the man skilled in the art, as described for example by Murray, P. R. et al. in Manuel of Clinical Microbiology, 2007, 9th edition, and in particular in Vol. I, Section III, chapters 15 and 16 for bacteria and yeasts, Vol. II, Section VI, chapter 82 for viruses, and Vol. II, Section X, chapter 135 for protozoans. By way of example of conventional identification methods, the determination of the biological profile can be cited, using for example the Vitek 2 identification cards (bioMérieux), or using techniques of molecular biology with identification criteria based on investigating the presence of certain genes, and their sequence.

Identification can be performed directly from the sample in which the identification is effected, or the microorganisms contained in the sample can be cultured by methods well-known to the man skilled in the art with optimal culture media and culture conditions suited to the species of microorganisms to be researched, as described by Murray P. R. et al. in Manuel of Clinical Microbiology, 2007, $9^{th}$ edition, Vol. I, Section III, chapter 14, and in particular in Vol. I, Section IV, chapter 21 for bacteria, Vol. II, Section VI, chapter 81 for viruses, Vol. II, Section VIII, chapter 117 for yeasts, and Vol. II, Section X, chapter 134 for protozoans.

Thus, generally, in the case of identification by a biochemical method of a bacterium in a sample, it is firstly necessary to obtain it in pure culture, for example after seeding on agar-agar. Molecular biology (PCR) can in certain cases be applied directly to the sample to be analysed.

Instead of culturing the microorganisms, the latter can be concentrated by capture directly from the sample by means of active surfaces. Such a method has been described by W.-J. Chen et al. who have captured different bacterial species by means of magnetic beads with a surface activated with $Fe_3O_4/TiO_2$. Capture by other means is also possible, such as capture by lectins or by antibodies or by Vancomycin Capture permits concentration of the microorganisms and thus reduction or even elimination of the culture step. This results in a considerable saving in time.

Identification can also be performed by mass spectrometry, according to the techniques described above, preferably by MS, by MS/MS, or by MS followed by spectrometry of MS/MS type, which constitutes an embodiment of the invention. In this case also, the sample can be previously subjected to a culture step such as seeding on agar-agar.

The use of an identification method by MS is advantageous as it can be performed in a few minutes and it requires a mass spectrometer with a single analyser, i.e. a less complex instrument than a tandem mass spectrometer used in MS/MS.

The use of an identification method by MS followed by spectrometry of MS/MS type is also advantageous. It allows the identity of the ions observed under MS to be ascertained, which increases the specificity of the analysis.

The use of an identification method by MS/MS of MRM type has the advantage of being more sensitive and more simple than the conventional MS and then MS/MS approaches. This method requires neither high-performance software to process the information between the acquisition of the MS spectrum and of the MS/MS spectrum, nor changing of the settings of the machine parameters to link the MS and then MS/MS spectra.

The identification method by MS can be performed with an electrospray source on the raw sample, as described by S. Vaidyanathan et al. or by R. Everley et al. after chromatographic separation. Different m/z ranges then permit identification of the organisms. S. Vaidyanathan et al. have used a window between 200 and 2000 Th and R. Everley et al. a window between 620 and 2450 Th. The mass spectra can also be deconvolved to access the mass of the proteins regardless of their state of charge. R. Everley et al. have thus exploited masses between approximately 5 000 and 50 000 Da. Alternatively, the method of identification by MS can also be performed by means of a MALDI-TOF, as described by Claydon et al and T. Krishnamurthy and P. Ross The analysis associates the acquisition of a mass spectrum and the interpretation of expert software. It is extremely simple and can be performed in a few minutes. This method of identification is currently becoming widespread in medical analysis laboratories The identification of bacteria by MS and then MS/MS via their proteins present in the sample has been widely applied by many teams. As an example, it is possible to cite the recent works of Manes N. et al. who have studied the peptidome of *Salmonella enterica*, or the works of R. Nandakumar et al. or of L. Hernychova et al. who have studied the proteome of bacteria after digestion of the proteins with trypsin. The conventional approach consists in i) acquiring an MS spectrum, ii) successively selecting each precursor ion observed in the MS spectrum with an intense signal, iii) successively fragmenting each precursor ion and acquiring its MS/MS spectrum, iv) interrogating protein databases such as SWISS-PROT or NCBI, through software such as Mascot (Matrix Science, London, United Kingdom) or SEQUEST (Thermo Scientific, Waltham, United States of America), to identify the peptide having a high probability of corresponding to the MS/MS spectrum observed. This method can lead to the identification of a microorganism if a protein or a peptide characteristic of the species is identified.

According to yet another embodiment, the identification of said at least one microorganism is performed by a conventional identification method and the method of the invention comprises an additional step of confirmation of the identification of said at least one microorganism, which confirmation step is performed by mass spectrometry, according to the techniques described above for the identification of microorganisms.

According to a particular embodiment, the mass spectrometry of the confirmation step is mass spectrometry of MS/MS type, preferably MRM.

One of the advantages of the use of mass spectrometry resides in the fact that it is particularly useful for quantifying molecules, in the present case the markers of the properties of typing, resistance to at least one antimicrobial. For this purpose, use is made of the detected current intensity, which is proportional to the quantity of the target molecule. The current intensity thus measured can serve for quantitative measurement permitting determination of the quantity of target molecule present, which is characterised by its expression in International System of units (SI) of $mol/m^3$ or $kg/m^3$ type, or by multiples or sub-multiples of these units, or by the usual derivatives of the SI units, including their multiples or sub-multiples. As a non-limiting example, units such as ng/ml or fmol/l are units characterising a quantitative measurement.

Calibration is nevertheless necessary to be able to correlate the measured area of the peak, corresponding to the current intensity induced by the detected ions, with the quantity of target molecule to be assayed. For this purpose, the calibrations conventionally used in mass spectrometry can be performed, within the framework of the invention. MRM assays are conventionally calibrated by means of external standards or, preferably, by means of internal standards such as described by T. Fortin et al. In the case in which the target molecule is a proteotypic peptide, permitting assay of a protein of interest, the correlation between the quantitative measurement and the quantity of target proteotypic peptide, and therefore of protein of interest, is obtained by calibrating the measured signal relative to a calibration signal for which the quantity to be assayed is known. The calibration can be performed by means of a calibration curve, for example obtained by successive injections of calibration proteotypic peptide at different concentrations (external calibration), or in preferred manner, by internal calibration using a heavy peptide, as an internal standard, for example according to the AQUA, QconCAT or PSAQ methods detailed below. By "heavy peptide" is understood a peptide corresponding to the proteotypic peptide, but in which one or more atoms of carbon 12 ($^{12}C$) is (are) replaced by carbon 13 ($^{13}C$), and/or one or more atoms of nitrogen 14 ($^{14}N$) is (are) replaced by nitrogen 15 ($^{15}N$).

The use of heavy peptides, as internal standards (AQUA), has also been proposed in patent application US 2004/0229283. The principle is to artificially synthesise proteotypic peptides with amino acids including isotopes heavier than the usual natural isotopes. Such amino acids are obtained, for example, by replacing certain of the carbon 12 ($^{12}C$) atoms with carbon 13 ($^{13}C$), or by replacing certain of the nitrogen 14 ($^{14}N$) atoms with nitrogen 15 ($^{15}N$). The artificial (AQUA) thus synthesised has exactly the same physicochemical properties as the natural peptide (with the exception of a higher mass). It is generally added, at a given concentration, to the sample upstream of the assay by mass spectrometry, for example between the treatment causing cleavage of the proteins of the sample of interest and the fractionation of the peptides obtained after the treatment step. As a result, the AQUA peptide is co-purified with the natural peptide to be assayed, on fractionation of the peptides. The two peptides are therefore injected simultaneously into the mass spectrometer, for assay. They are then subject to the same ionisation yields in the source. The comparison of the peak areas of the natural peptides and AQUA, the concentration of which is known, permits calculation of the concentration of the natural peptide thereby determining the concentration of the protein to be assayed. A modification of the AQUA technique has been proposed by J.-M. Pratt et al. under the name of QconCat. This modification is also described in patent application WO 2006/128492. It consists in concatenating different AQUA peptides and producing the artificial polypeptide in the form of heavy recombinant protein. The recombinant protein is synthesised with amino acids including heavy isotopes. In this manner, it is possible to obtain a standard for calibrating the simultaneous assay of several proteins at lesser cost. The QconCAT standard is added at the start, upstream of the treatment causing the cleaving of the proteins and before the steps of fractionation of the proteins, of denaturation, of reduction and then locking of the thiol functions of the proteins, if these are present. The QconCAT standard is therefore subject to the same treatment cycle causing the cleaving of the proteins as the natural protein, which permits taking into account the yield of the treatment step causing the cleaving of the proteins. Indeed, the treatment, particularly by digestion, of the natural protein can be incomplete. In this case the use of an AQUA standard would lead to an under-estimation of the quantity of natural protein. For an absolute assay, it can therefore be important to take into account the yields of the treatment causing the cleaving of the proteins. However, V. Brun et al. have shown that, sometimes, the QconCAT standards did not exactly reproduce the treatment yield, particularly by digestion of the natural protein, doubtless due to the fact of different three-dimensional conformation of the QconCAT protein.

V. Brun et al. have then proposed the use of a method termed PSAQ and described in patent application WO 2008/145763. In this case, the internal standard is a recombinant protein, having the same sequence as the natural protein but synthesised with heavy amino acids. The synthesis is performed ex-vivo with heavy amino acids. This standard has strictly the same physicochemical properties as the natural protein (with the exception of a higher mass). It is added at the start, before the step of fractionation of the proteins, when the latter is present. It is therefore co-purified with the native protein, at the step of fractionation of the proteins. It has the same treatment yield, particularly by digestion, as the native protein. The heavy peptide obtained after cleavage is also co-purified with the natural peptide, if a step of fractionation of the peptides is performed. The two peptides are therefore injected simultaneously into the mass spectrometer, to be quantitatively assayed. They are subject to the same ionisation yields in the source. The comparison of peak areas of the natural peptides and of the reference peptides in the PSAQ method permits calculation of the concentration of protein to be assayed taking into account all of the steps of the assay method.

All of these techniques, i.e. AQUA, QconCAT or PSAQ or any other calibration technique, used in assays by mass spectrometry and in particular in MRM or MS assays, could be employed to perform the calibration.

BIBLIOGRAPHIC REFERENCES

W.-J. Chen et al., 2008, Anal. Chem., 80: 9612-9621
T. Fortin et al., 2009, Mol. Cell Proteomics, 8(5): 1006-1015.
H. Keshishian et al., 2007, Mol. Cell Proteomics, 2212-2229.
V. Fusaro et al., 2009, Nature Biotech. 27, 190-198.
J. Mead et al., 15 Nov. 2008, Mol. Cell Proteomics, E-pub.
F. Desiere et al., 2006, Nucleic Acids Res., 34(database issue): D655-8).
S. Vaidyanathan et al., 2001, Anal. Chem., 73: 4134-4144.
R. Everley et al., 2009, J. Microbiol. Methods, 77: 152-158.
M. Claydon et al, 1996, Nature Biotech. 14: 1584-1586.
T. Krishnamurthy & P. Ross, 1996, Rapid Com. Mass Spec., 10: 1992-1996.
Manes N. et al., 2007, Mol. & Cell. Proteomics, 6(4): 717-727.
R. Nandakumar et al., 2009, Oral Microbiology Immunology, 24: 347-352).
L. Hernychova et al., 2008, Anal. Chem., 80: 7097-7104.
J.-M. Pratt et al., 2006, Nat. Protoc., 1: 1029-1043.
V. Brun et al., 2007, Mol. Cell Proteomics, 2139-2149.
D. Lopez-Ferrer et al., 2008, Anal. Chem., 80: 8930-8936
D. Lopez-Ferrer et al., 2005, J. Proteome res., 4(5): 1569-1574
Gaskell, Electrospray: principles and practise, 1997, J. Mass Spectrom., 32, 677-688).
L. Anderson & C. Hunter, 2006, Mol. Cell Proteomics, 573-588).
B. Han & R. Higgs, 2008, Brief Funct Genomic Proteomic., 7(5): 340-54).
K.-Y. Wang et al., 2008, Anal Chem, 80(16) 6159-6167).
J. Bundy & C. Fenselau, 1999, Anal. Chem. 71: 1460-1463.
K-C Ho et al., 2004, Anal. Chem. 76: 7162-7268.
Y. S. Lin et al., 2005, Anal. Chem., 77: 1753-1760.
P. Seng et al., 2009, Clin. Infect. Dis., 49: 543-551.

The invention claimed is:

1. A method of obtaining peptides from procaryotic and/or eucaryotic cells, the method comprising:
   a) lysis of the procaryotic and/or eucaryotic cells and recovery of the proteins thus obtained;
   b) denaturation of the proteins using at least one denaturing agent;
   c) alkylation of the denatured proteins using at least one alkylating agent;
   d) enzymatic proteolysis of the proteins obtained at the end of step c) using at least one proteolytic enzyme;
   e) recovery of the peptides obtained at the end of the enzymatic proteolysis step d), in which the lysis of the procaryotic and/or eucaryotic cells in step a) is a lysis at a low concentration of chaotropic agent(s);
   and in which at least steps a) and b) are performed simultaneously;
   the lysis at a low concentration of chaotropic agent(s) being carried out at a concentration of chaotropic agent(s) less than or equal to 1 M; and
   the method being implemented under a pressure below 100 bar.

2. The method according to claim 1, in which the lysis at a low concentration of chaotropic agent(s) is carried out in the absence of non-saline chaotropic agent(s).

3. The method according to claim 1, in which the lysis at a low concentration of chaotropic agent(s) is a lysis by sonication performed by means of an ultrasound probe.

4. The method according to claim 3, in which the ultrasound probe is not subjected to a preheating step prior to lysis by sonication.

5. The method according to claim 1, in which the proteolytic enzyme is a serine protease selected from the group consisting of trypsin, chymotrypsin and elastase.

6. The method according to claim 1, in which the denaturing agent is a thiol-reducing agent, selected from 2-mercaptoethanol, tris(2-carboxyethyl)phosphine, dithioerythritol, tributylphosphine and dithiothreitol.

7. The method according to claim 1, in which the alkylating agent is selected from the group formed by N-ethylmaleimide, iodoacetamide and M-biotin.

8. The method according to claim 1, in which the minimum duration corresponding to the step of proteolysis d) is approximately 15 minutes.

9. The method according to claim 1, in which at least steps a)-c) are performed simultaneously.

10. The method according to claim 1, in which steps a)-d) are performed simultaneously.

11. The method according to claim 9, in which:
   the denaturing agent is a thiol-reducing agent selected from tris(2 carboxyethyl)phosphine and dithiothreitol; and
   the alkylating agent is iodoacetamide.

12. The method according to claim 1, the method being implemented under atmospheric pressure.

13. The method of analysis of peptides of procaryotic and/or eucaryotic cells comprising:
   i) obtaining peptides from the procaryotic and/or eucaryotic cells using the method according to claim 1; and
   ii) analysis of the peptides thus obtained, the analysis being performed using an analysis means of mass spectrometry type.

14. The method according to claim 1, in which the concentration of chaotropic agent(s) is less than or equal to 100 mM.

15. The method according to claim 1, in which the pressure is less than 50 bar.

16. The method according to claim 1, in which the pressure is less than 10 bar.

* * * * *